US011231423B2

(12) United States Patent
Sanada et al.

(10) Patent No.: US 11,231,423 B2
(45) Date of Patent: *Jan. 25, 2022

(54) METHOD AND KIT FOR THE DETECTION OF BILIARY TRACT CANCER

(71) Applicants: TORAY INDUSTRIES, INC., Tokyo (JP); NATIONAL CANCER CENTER, Tokyo (JP)

(72) Inventors: Mitsuaki Sanada, Kamakura (JP); Michimoto Kobayashi, Kamakura (JP); Aiko Takayama, Kamakura (JP); Yoshiyuki Sasajima, Kamakura (JP); Giman Jung, Kamakura (JP); Tesshi Yamada, Tokyo (JP); Kazufumi Honda, Tokyo (JP)

(73) Assignees: TORAY INDUSTRIES, INC., Tokyo (JP); NATIONAL CANCER CENTER, Tokyo (JP)

( * ) Notice: Subject to any disclaimer, the term of this patent is extended or adjusted under 35 U.S.C. 154(b) by 297 days.

This patent is subject to a terminal disclaimer.

(21) Appl. No.: 15/546,178

(22) PCT Filed: Jan. 25, 2016

(86) PCT No.: PCT/JP2016/052023
§ 371 (c)(1),
(2) Date: Jul. 25, 2017

(87) PCT Pub. No.: WO2016/121695
PCT Pub. Date: Aug. 4, 2016

(65) Prior Publication Data
US 2018/0017564 A1    Jan. 18, 2018

(30) Foreign Application Priority Data
Jan. 26, 2015 (JP) .............................. JP2015-012667

(51) Int. Cl.
*G01N 33/574*  (2006.01)
*G01N 33/577*  (2006.01)
*G01N 33/53*   (2006.01)
*C07K 16/18*   (2006.01)

(52) U.S. Cl.
CPC ....... *G01N 33/57446* (2013.01); *C07K 16/18* (2013.01); *G01N 33/53* (2013.01); *G01N 33/574* (2013.01); *G01N 33/577* (2013.01); *C07K 2317/565* (2013.01); *G01N 2333/775* (2013.01)

(58) Field of Classification Search
CPC .......... G01N 33/57446; G01N 33/577; G01N 33/53; G01N 33/574; G01N 2333/775; C07K 16/18; C07K 2317/565
See application file for complete search history.

(56) References Cited

U.S. PATENT DOCUMENTS

| 5,714,350 | A  | 2/1998  | Sung et al.       |
|-----------|----|---------|--------------------|
| 6,350,861 | B1 | 2/2002  | Co et al.          |
| 2008/0248500 | A1 | 10/2008 | Semmes et al.    |
| 2010/0130375 | A1 | 5/2010  | Ataman-Onal et al. |
| 2016/0245815 | A1 | 8/2016  | Sanada et al.     |

FOREIGN PATENT DOCUMENTS

| JP | 2001289861 A      | 10/2001 |           |
|----|-------------------|---------|-----------|
| JP | 2002323499 A      | 11/2002 |           |
| JP | 2008527351 A      | 7/2008  |           |
| JP | 2009034071 A      | 2/2009  |           |
| JP | 2010175452 A      | 8/2010  |           |
| JP | 2010533855 A      | 10/2010 |           |
| WO | 9002809 A1        | 3/1990  |           |
| WO | 9713844 A1        | 4/1997  |           |
| WO | WO 2007/133957 A1 * | 11/2007 |         |
| WO | WO-2007133957 A1 * | 11/2007 | ........... C12Q 1/6886 |
| WO | 2015050107 A1     | 4/2015  |           |
| WO | 2015050107 A1     | 3/2017  |           |

OTHER PUBLICATIONS

Honda et al. Plasma biomarker for detection of early stage pancreatic cancer and risk factors for pancreatic malignancy using antibodies for apolipoprotein—AII isoforms. (Scientific Reports 5: 1-15, published Nov. 9, 2015).*
International Search Report and Written Opinion for International Application No. PCT/JP2016/052023, dated Apr. 12, 2016—6 Pages 2017.
Blanco-Vaca F., et al., "Role of apoA-II in lipid metabolism and atherosclerosis: advances in the study of an enigmatic protein", J. Lipid Res., 42: 1727-1739 (2001).
Dan H. Moore II, "Book Review of 'Classification and Regression Trees' by Leo Breinman, et al. Brooks/Cole Publishing, Montery, 1984, 358 pages", Cytometry 8:534-535 (1987).
Breiman, L., "Random Forests", Machine Learning, 45: 5-32 (2001).
Breiman, L.,, "Statistical Modeling: The Two Cultures", Statistical Science, vol. 16, No. 3, pp. 199-231 (2001).
Felgner et al., "Llipofection: A highly efficient, lipid-mediated DNA-transfection procedure", Proc. Natl. Acad. Sci. USA, vol. 84—pp. 7413-7417 (1987).
Green, M. et al., Molecular Cloning: A Laboratory Manual (4th ed.), Cold Spring Harbor Laboratory Press, Cold Spring Harbor, New York—pp. 1-34 (2012).
Holliger et al., "Diabodies": Small bivalent and bispecific antibody fragments, Proc. Natl. Acad. Sci. USA, 90: 6444-6448 (1993).
Honda et al., "Altered Plasma Apolipoprotein Modifications in Patients with Pancreatic Cancer: Protein Characterization and Multi-Institutional Validation", Pios One, Oct. 2012, vol. 7, Issue 10, e46908, pp. 1-11 (2012).

(Continued)

*Primary Examiner* — Alana Harris Dent
(74) *Attorney, Agent, or Firm* — RatnerPrestia

(57) ABSTRACT

The present invention provides a method for detecting biliary tract cancer by measuring the amounts of APOA2 protein variants in a test sample with anti-APOA2 antibodies, the anti-APOA2 antibodies for use in the above method and a detection kit for biliary tract cancer including the above antibodies.

14 Claims, 4 Drawing Sheets

Specification includes a Sequence Listing.

(56) References Cited

OTHER PUBLICATIONS

PDB; Protein Data Bank; http://www.rcsb.org/pdb/home.do (2017).

Japanese Society of Hepato-Biliary-Pancreatic Surgery and Japan Society of Clinical Oncology, Evidence-based Clinical Practice Guidelines on Biliary tract cancer (1st ed.),—2 Pages (2013) (with partial translation).

Junghans et al., "Anti-Tac-H, a Humanized Antibody to the Interleukin 2 Receptor with New Features for Immunotherapy in Malignant and Immune Disorders", Cancer Research 50: 1495-1502 (1990).

Marvin et al., "Recombinant approaches to IgG-like bispecific antibodies", Acta Pharmacol. Sin., 26: 649-658 (2005).

Olafson et al., "Covalent disulfide-linked anti-CEA diabody allows site-specific conjugation and radiolabeling for tumor targeting applications", Prot. Engr. Des. Sel., 17: 21-27 (2004).

Pankhurst G., et al., "Characterization of a specifically oxidized apolipoproteins in mildly oxidized high density lipoprotein", J. Lipid Res., 44: 349-355 (2003).

Rocco AG., et al., "A Model Structure for the Heterodimer apoA-IMilano-apoA-ll Supports Its Peculiar Susceptibility to Proteolysis", Biophys. J., 91: 3043-3049 (2006).

Ruczinski, I.et al., "Logic Regression", Journal of Computational and Graphical Statistics, 12: 475-511 (2003).

Wright et al., "Effect of C2-Associated Carbohydrate Structure on Ig Effector Function: Studies with Chimeric Mouse-Human IgG1 Antibodies in Glycosylation Mutants of Chinese Hamster Ovary Cells", Journal of Immunology, 160: 3393-3402 (1998).

* cited by examiner

METHOD AND KIT FOR THE DETECTION OF BILIARY TRACT CANCER

CROSS REFERENCE TO RELATED APPLICATIONS

This is the U.S. National Phase application of PCT International Application No. PCT/JP2016/052023, filed Jan. 25, 2016, and claims priority to Japanese Patent Application No. 2015-012667, filed Jan. 26, 2015, the disclosures of these applications being incorporated herein by reference in their entireties for all purposes.

FIELD OF THE INVENTION

The present invention relates to a method for detecting biliary tract cancer, the method comprising measuring the amounts of APOA2 protein variants in a test sample with antibodies that specifically bind to the APOA2 protein (i.e., anti-APOA2 antibody), and a detection kit for biliary tract cancer including the anti-APOA2 antibody.

BACKGROUND OF THE INVENTION

According to the statistics of 2012, cancer is the leading cause of death in Japan. Cancers are derived from normal tissues and characterized by tumor mass formation due to an abnormal proliferation of tumor cells, infiltration of tumor mass-forming cancer cells into adjacent tissues and distant metastasis through blood and lymph vessels to various organs. It has been known that the concentration of various proteins in body fluid of a patient, such as blood and urine, fluctuates during the onset and progression of cancers as described above. Such proteins are called tumor markers (cancer detection markers) and expected to be applied for various clinical practices including early detection of cancer, post-treatment follow-up and the like (for example, Patent Literature 1 to 3). However, a problem was that many conventional tumor markers used in clinical diagnosis had a low positive rate and most tumor markers demonstrated the false negative results, particularly in respect of early stage cancer. Moreover, another problem was that diagnostic targets of some tumor markers, like "CA19-9" (Carbohydrate Antigen 19-9), were restricted to particular patients such as sialyl Lewis-A antigen-positive patients (Non-Patent Literature 1).

Since advanced or terminal cancer, characterized by infiltration into adjacent tissues and/or distant metastasis, has a poor prognosis, early detection is important in the effective treatment of cancer. Therefore, there is an expectation for highly sensitive tumor markers available for the detection of early stage cancers and applicable, without limitation, to any patients as diagnostic targets to be identified.

The term biliary tract cancer refers to all kinds of tumors occurring in the biliary tract. Biliary tract cancer is known to be one of the intractable cancers, among many cancers, and there have been no effective treatment modalities established other than surgery and, thus, early detection and prevention before onset of the disease will be particularly important. Blood biochemistry, CT, magnetic resonance instrument (MRI), endoscopic ultrasonography (EUS) and the like are used as the diagnosis methods for biliary tract cancer (Non-Patent Literature 1). However, biliary tract cancer has no obvious symptoms in its early stage and is often diagnosed at an advanced stage and, consequently, it is generally difficult to treat. Accordingly, a new diagnostic technology that enables biliary tract cancer to be detected in an accurate and simple manner is required to be established.

APOA2 (Apolipoprotein A2, or Apolipoprotein A-II) protein (GenBank accession No. NP_001634.1) is a member of apolipoprotein family, which composes plasma lipoproteins. Ten or more apolipoproteins have been identified so far and the major functions of those proteins are to stabilize the lipoprotein structure, to activate the enzymes involved in the lipoprotein metabolism, to function as a ligand to the lipoprotein receptor on the cell surface, and the like. The APOA2 protein is synthesized in liver tissues as a precursor consisting of 100 amino acids including the signal peptide. The processed mature form present in blood consists of 77 amino acids. The mature form of the APOA2 protein is one of the apolipoproteins of high density lipoproteins (HDL), which has a glutamine residue (Q) at the amino-terminus (N-terminus), a threonine residue (T) at position 76 from the N-terminus and a glutamine residue (Q) at position 77 corresponding to the carboxyl-terminus (C-terminus). Moreover, it is reported that three APOA2 protein variants having different masses are present, such as the APOA2-ATQ protein which is the full-length APOA2 protein, the APOA2-AT protein which is an APOA2 protein with deletion of the C-terminal glutamine residue (Q), and the APOA2-A protein which is an APOA2 protein with deletion of the C-terminal threonine and glutamine residues (TQ) (Non-Patent Literature 2).

According to an analysis based on the three dimensional structural data of the APOA2 protein (PDB ID: 1L6L) recorded in a protein structure databank (PDB; Protein Data Bank; http://www.rcsb.org/pdb/home.do), APOA2 proteins form a dimer through a disulfide (S-S) bond between cysteine residues located in the N-terminal region. Thus, it is understood that APOA2 proteins are present in blood as dimers having different molecular weights depending on the combination of the above-described three variants. Specifically, a dimer composed of the full-length APOA2-ATQ proteins (the APOA2-ATQ/ATQ protein dimer), a dimer composed of the APOA2-ATQ protein and the APOA2-AT protein (the APOA2-ATQ/AT protein dimer), a dimer composed of the APOA2-AT proteins (the APOA2-AT/AT protein dimer), a dimer composed of the APOA2-AT protein and the APOA2-A protein (the APOA2-AT/A protein dimer), a dimer composed of the APOA2-A proteins (the APOA2-A/A protein dimer) and the like are known. Also, in addition, it is understood that the APOA2 protein forms dimers with other proteins, such as the APOD protein, the APOE protein and the APOA1-M protein, through disulfide linkage or, otherwise, is present as a monomer (Non-Patent Literature 3 and 4).

In an attempt to detect biliary tract cancer by mass spectrometry through the detection of APOA2 as a cancer detection marker, it has been indicated that a low performance in the discrimination of biliary tract cancer patient and healthy subject is shown and the sensitivity remains at 57% (at a specificity of 97%) even in the detection method combined with the detection of another cancer detection marker, APOCIII (Non-Patent Literature 5). Thus, it has been expected in the art that the discrimination of healthy subject and biliary tract cancer patient would be more difficult due to further reduction of the accuracy in detection of biliary tract cancer when the APOA2 dimers alone are just used as markers for biliary tract cancer. Moreover, three complicated steps including the measurement with a mass spectrometer are required to gain the above-described sensitivity. For example, blood samples used in mass spectrometry must be pretreated with 9 M urea, 2% CHAPS and the like in the first step. However, a solution containing urea should be freshly prepared each measurement time to satisfy uniform pretreatment conditions because urea is easily degraded and is not suitable for long-term preservation. Moreover, in the following step, the pretreated samples must be captured on the surface of protein chips (manufactured by Ciphergen Biosystems Inc.). It is understood that the capture efficiency is greatly influenced by washing conditions and the preparation conditions for reagents because the properties on the surface of the protein chips, such as charge state and hydrophobicity, are used for adsorption in this capture step. In the final step, the captured samples are measured with a mass spectrometer. However, relevant skills are required for the operation of mass spectrometers, for example, in the adjustment of laser intensity. Moreover, mass spectrometers are low throughput in nature, in the handling of samples. Furthermore, in cases where many different proteins are contained in a sample, signals derived from those proteins interfere with each other, resulting in the assignment of the signals being difficult. In addition, problems remain in quantitative measurement, suggesting that this method is unsuitable for diagnostic uses that require highly accurate measurements. Accordingly, there was a high barrier problem that prevented the practical use of the method.

ELISA is known to be a low-cost and practical method, characterized by being higher throughput in nature, in the evaluation many samples, as compared with mass spectrometry. Moreover, ELISA is such a commonly used procedure that fewer skills are required for the operation. Furthermore, the use of two antibodies in ELISA delivers quite specific results, which allows highly reproducible measurements using a standard reference substance. Thus, a comprehensive and quantitative analysis of APOA2 protein variants present in samples and with different molecular weights can be achieved.

Patent Literature

Patent Literature 1: JP Patent Publication (Kokai) No. 2001-289861.
Patent Literature 2: JP Patent Publication (Kokai) No. 2002-323499.
Patent Literature 3: JP Patent Publication (Kokai) No. 2009-034071.

Non-Patent Literature

Non-Patent Literature 1: Evidence-based Clinical Practice Guidelines on Biliary tract cancer (1st ed.), 2013, Japanese Society of Hepato-Biliary-Pancreatic Surgery and Japan Society of Clinical Oncology, eds., Igaku Tosho-Shuppan Ltd.
Non-Patent Literature 2: Pankhurst G., et al., 2003, J. Lipid Res., 44: 349-355.
Non-Patent Literature 3: Blanco-Vaca F., et al., 2001, J. Lipid Res., 42: 1727-1739.
Non-Patent Literature 4: Rocco AG., et al., 2006, Biophys. J., 91: 3043-3049.
Non-Patent Literature 5: Honda K., et al., 2012, PLoS One, 7: e46908.

SUMMARY OF THE INVENTION

Tumor markers are generally used for the detection of tumors but hardly detect biliary tract cancer. Then, there was a problem that early detection of biliary tract cancer with tumor markers was very difficult.

An object of the present invention is to provide a detection method and a detection kit for biliary tract cancer, wherein the use of APOA2 protein variants as markers for biliary tract cancer allows the detection method to be a simpler and higher throughput alternative to the detection method described in Non-Patent Literature 5 and to achieve a high performance in the detection of biliary tract cancer.

According to exemplary embodiments, the present invention provides for a method to measure separately the total amount of the APOA2-ATQ protein and the total amount of the APOA2-AT protein, the method adopting a sandwich ELISA in which anti-APOA2 protein terminus antibodies specifically binding to the C-terminal region of either the APOA2-ATQ protein or the APOA2-AT protein and an antibody specifically binding to the APOA2 proteins except their C-terminal regions (an anti-APOA2 protein non-terminus antibody) are used in combination. Furthermore, a method to discriminate biliary tract cancer patients and normal subjects with high accuracy by using an analytical method, in which the total amount of each protein is measured and the measurement results are combined, was established. The inventors found the ability to detect biliary tract cancer with quite high sensitivity based on this technology and thereby completed the present invention.

Exemplary embodiments of the present invention include:
(1) A method for detecting biliary tract cancer by the amounts of APOA2 protein variants in a body fluid sample from a test subject, the method comprising: (A) a first step of measuring the amount of the APOA2-ATQ protein in the sample by using an anti-APOA2-ATQ terminus antibody which specifically binds to the C-terminal region of the APOA2-ATQ protein consisting of the amino acid sequence represented by SEQ ID NO: 1, and an anti-APOA2-ATQ non-terminus antibody which binds to the amino acid sequence excluding said C-terminal region; (B) a second step of measuring the amount of the APOA2-AT protein in the sample by using an anti-APOA2-AT terminus antibody which specifically binds to the C-terminal region of the APOA2-AT protein consisting of the amino acid sequence represented by SEQ ID NO: 2, and an anti-APOA2-AT non-terminus antibody which binds to the amino acid sequence excluding said C-terminal region; and (C) a third step of determining that the test subject is affected with biliary tract cancer when the discriminant value is statistically significantly different compared to the discriminant value of a normal subject, wherein a discriminant value is obtained by inputting the amount of the APOA2-ATQ protein obtained in the first step and the amount of the APOA2-AT protein obtained in the second step into a prescribed discriminant function.
(2) The detection method according to (1), wherein the C-terminal regions of the APOA2-ATQ protein and the APOA2-AT protein comprise a sequence consisting of 6 or more consecutive amino acids including the C-terminus of the corresponding protein.
(3) The detection method according to (1) or (2), wherein the discriminant function is any one selected from the group consisting of a logistic regression equation, a formula generated by support vector machine analysis, a formula generated by neural network analysis, and a formula generated by discriminant analysis.
(4) The detection method according to (3), wherein the discriminant function expressed as a logistic regression equation is any one of:

$$a \times (APOA2\text{-}ATQ) + b \times (APOA2\text{-}AT) + d, \quad \text{Formula 1:}$$

$$a \times (APOA2\text{-}ATQ) + b \times (APOA2\text{-}AT) + c \times [(APOA2\text{-}ATQ) \times (APOA2\text{-}AT)] + d, \quad \text{Formula 2:}$$

$$c \times [(APOA2\text{-}ATQ) \times (APOA2\text{-}AT)] + d, \quad \text{Formula 3:}$$

wherein each of a, b, c and d is an optional real number except zero, APOA2-ATQ represents the measured value of the APOA2-ATQ protein, and APOA2-AT represents the measured value of the APOA2-AT protein.

(5) The detection method according to (4), wherein the discriminant value of the test subject obtained by the discriminant function is two thirds or less of the discriminant value of the normal subject.

(6) The detection method according to any of (1) to (5), wherein the body fluid sample is blood.

(7) The detection method according to any of (1) to (6), wherein the biliary tract cancer is early biliary tract cancer.

(8) A kit for the detection of biliary tract cancer, comprising one or more of a monoclonal antibody or a fragment thereof selected from the group consisting of an anti-APOA2-ATQ terminus monoclonal antibody or a fragment thereof and an anti-APOA2 protein non-terminus monoclonal antibody or a fragment thereof, wherein the anti-APOA2-ATQ terminus monoclonal antibody has the CDR1, CDR2 and CDR3 of the heavy chain consisting of the amino acid sequences represented by SEQ ID NOs: 4, 5 and 6, or SEQ ID NOs: 10, 11 and 12, respectively, and the CDR1, CDR2 and CDR3 of the light chain consisting of the amino acid sequences represented by SEQ ID NOs: 7, 8 and 9, or SEQ ID NOs: 13, 14 and 15, respectively; and the anti-APOA2 protein non-terminus monoclonal antibody has the CDR1, CDR2 and CDR3 of the heavy chain consisting of the amino acid sequences represented by SEQ ID NOs: 16, 17 and 18 or SEQ ID NOs: 22, 23 and 24, respectively, and the CDR1, CDR2 and CDR3 of the light chain consisting of the amino acid sequences represented by SEQ ID NOs: 19, 20 and 21, or SEQ ID NOs: 25, 26 and 27, respectively.

The present specification incorporates the disclosure of Japanese Patent Application No. 2015-012667, which is the basis of priority of this application.

According to embodiments of the present invention, the measurement of APOA2 protein variants as markers for biliary tract cancer in the blood collected from patients can lead to simple, high throughput and highly sensitive detection of biliary tract cancer. For example, just by measuring the amounts of certain APOA2 protein variants contained in a body fluid sample, such as blood, collected from any patient, it can be determined whether or not the patient has biliary tract cancer, or the risk of biliary tract cancer in the patient can be evaluated.

DETAILED DESCRIPTION OF THE INVENTION

Figure 1:
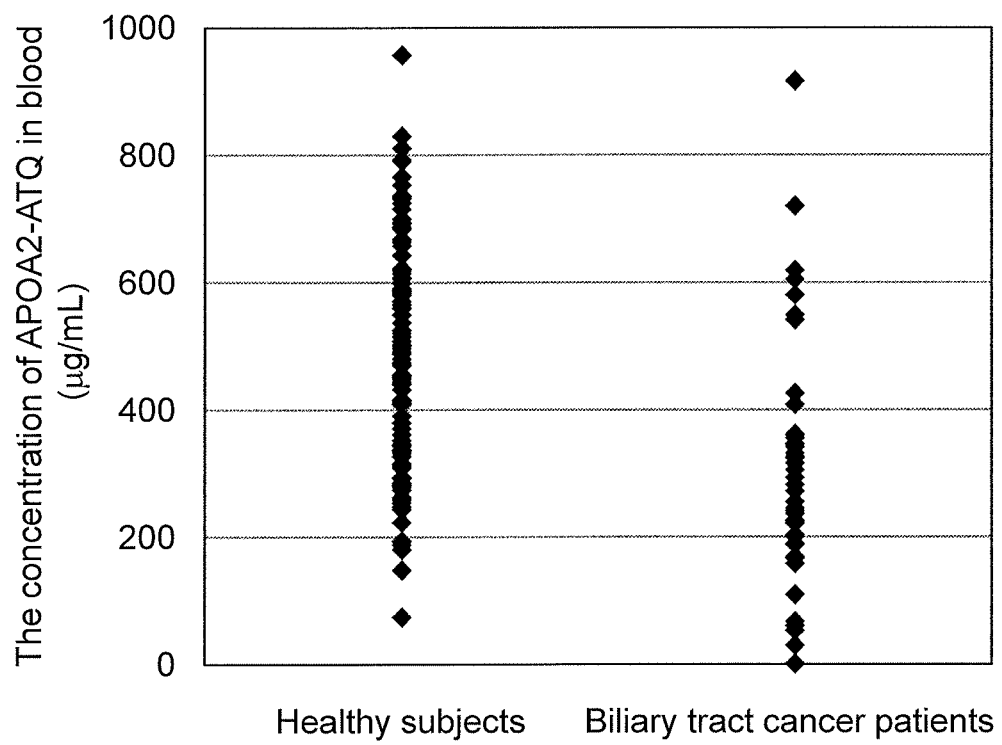
FIG. 1 shows a measurement of the concentration of the APOA2-ATQ protein contained in the plasma from 44 biliary tract cancer patients and 109 healthy subjects by sandwich ELISA using a monoclonal antibody specifically recognizing an amino acid sequence of the C-terminal region of the APOA2-ATQ protein (anti-APOA2-ATQ terminus monoclonal antibody) and an antibody specifically recognizing the amino acid sequence excluding the C-terminal region (anti-APOA2-ATQ non-terminus antibody).

The subject of measurement according to embodiments of the present invention is biliary tract cancer. In this specification, the term "biliary tract cancer" refers to all kinds of malignant tumors occurring in the biliary tract where bile is allowed to run through and also stored, including cancers classified into extrahepatic bile duct cancer, intrahepatic bile duct cancer, gallbladder cancer, and papillary cancer (Evidence-based Clinical Practice Guidelines on Biliary tract cancer (1st ed.), 2013, Japanese Society of Hepato-Biliary-Pancreatic Surgery and Japan Society of Clinical Oncology, eds., Igaku Tosho-Shuppan Ltd., p. 62). The progress of biliary tract cancer targeted by embodiments of the present invention is not limited. Then, early stage cancer, advanced cancer, and terminal cancer are all encompassed.

In this specification, the term "early stage cancer" refers to tumors focally localized at the place where they originally occur and confined in the mucosa or muscle layer, or tumors grown through the muscle layer but still confined within the wall, or tumors confined within the muscle layer but having metastasis to nearby lymph nodes. Specifically, the term refers to tumors classified according to the staging system of UICC (Unio Internationalis Contra Cancrum) into stages 0, IA, IB, IIA and IIB (TNM Classification of Malignant Tumors (7th ed.), Japanese version, 2012, TNM Committee of Japan National Committee for UICC, ed., Kanehara & Co. Ltd.). Although biliary tract cancer is an intractable cancer having a very poor prognosis as mentioned above, potential early detection of biliary tract cancer could significantly increase the five year survival rate.

1. Anti-APOA2 Antibodies and Fragments Thereof

The first aspect of embodiments of the present invention is anti-APOA2 antibodies (including anti-APOA2 protein terminus antibodies and anti-APOA2 protein non-terminus antibodies) and fragments thereof.

1-1. Anti-APOA2 Antibodies

In this specification, the term "APOA2 protein" refers to the APOA2 protein of each species, preferably the APOA2 protein from human (GenBank accession No. NP_001634.1). Specific examples of the APOA2 protein include variants of the wild-type APOA2 protein derived from human and represented by SEQ ID NO: 1, 2 or 3, and, furthermore, naturally-occurring mutants thereof and fragments thereof.

In this specification, the term "variants" described above means different molecular forms of the APOA2 protein that can be present in plasma, serum, or other body fluid of human or animals. For example, the term refers to APOA2 proteins having a different structure in the C-terminal region or naturally-occurring mutants thereof. Specifically, the APOA2 protein variant refers to, for examples, the APOA2-

ATQ protein represented by SEQ ID NO: 1 and comprising the C-terminal region having an amino acid sequence that ends in ATQ, the APOA2-AT protein represented by SEQ ID NO: 2 and comprising the C-terminal region having an amino acid sequence that ends in AT, or the APOA2-A protein represented by SEQ ID NO: 3 and comprising the C-terminal region having an amino acid sequence that ends in A.

In this specification, the term "C-terminal region (carboxyl-terminal region)" refers to a region in an amino acid sequence, the region comprising the C-terminal amino acid and nearby several consecutive amino acids, in total, 6 to 25 amino acids, preferably 8 to 20 amino acids or 10 to 17 amino acids.

In this specification, the term "naturally-occurring mutant" refers to a mutant existing in the natural environment, such as a mutant having the amino acid sequence represented by SEQ ID NO: 1, 2, or 3 except that one or plural amino acids are deleted, substituted, or added, and a mutant having an amino acid sequence with an amino acid identity of 90% or more, 92% or more, or 94% or more, preferably 95% or more, more preferably 97% or more, further preferably 98% or more or 99% or more, to the above-described amino acid sequence. The term "amino acid identity" refers to the ratio (in percent) of the number of identical amino acid residues in one amino acid sequence to the total number of amino acid residues (including gaps) in the other amino acid sequence, when the two amino acid sequences are aligned with or without the introduction of gaps for maximum correspondence. The term "plural" refers to an integer from 2 to 10, such as an integer from 2 to 7, from 2 to 5, from 2 to 4, or from 2 to 3. Specific examples of the naturally-occurring mutants include mutants based on the polymorphisms such as SNPs (single nucleotide polymorphisms), splicing mutants (splicing variants) and the like. Moreover, the above-described substitution is preferably a conservative amino acid substitution. The conservative amino acid substitution is preferable because it allows a variant carrying that type of substitutions to have a structure and characteristics similar to those of the APOA2 proteins having the above-described amino acid sequences. Conservative amino acid means the relationship among amino acids classified into the same amino acid group. The following amino acid groups are known: non-polar amino acid group (glycine, alanine, phenylalanine, valine, leucine, isoleucine, methionine, proline, tryptophan), polar amino acid group (amino acids except for non-polar amino acids), charged amino acid group (acidic amino acid group (aspartic acid, glutamic acid) and basic amino acid group (arginine, histidine, lysine)), uncharged amino acid group (amino acids except for charged amino acids), aromatic amino acid group (phenylalanine, tryptophan, tyrosine), branched amino acid group (leucine, isoleucine, valine), and aliphatic amino acid group (glycine, alanine, leucine, isoleucine, valine), etc.

The term "fragments thereof" described above refers to fragments of the APOA2 protein variants and mutants thereof, including the C-terminal regions of the various APOA2 protein variants and naturally-occurring mutants thereof. Specifically, the term refers to protease digests of various APOA2 protein variants and mutants thereof.

Embodiments of the present invention provides anti-APOA2 protein terminus antibodies including an anti-APOA2-ATQ terminus antibody and an anti-APOA2-AT terminus antibody.

The term "anti-APOA2-ATQ terminus antibody" refers to an antibody or a fragment thereof that can specifically recognize and bind to an epitope located in the C-terminal region of the APOA2-ATQ protein. By the phrase "specifically recognize and bind to" is meant no or very low cross-reactivity with other APOA2 protein variants, which results in that the antibody cannot recognize and bind to or hardly binds to other APOA2 protein variants. Specifically, the term refers to an antibody that specifically binds to the C-terminal region of the APOA2-ATQ protein but not to the C-terminal region of the APOA2-AT protein and the C-terminal regions of the APOA2-A protein and the like. Such a terminus antibody may be either a polyclonal or monoclonal antibody, or a fragment thereof. Monoclonal antibodies are preferable to enable large-scale production and to achieve a uniform effect.

On the other hand, the term "anti-APOA2-AT terminus antibody" refers to an antibody or a fragment thereof that can specifically recognize and bind to an epitope located in the C-terminal region of the APOA2-AT protein. Specifically, the term refers to an antibody that specifically binds to the C-terminal region of the APOA2-AT protein but not to the C-terminal region of the APOA2-ATQ protein and the C-terminal regions of the APOA2-A protein and the like. Such a terminus antibody may be either a polyclonal or monoclonal antibody, or a fragment thereof. Monoclonal antibodies are preferable to enable large-scale production and to achieve a uniform effect.

Embodiments of the present invention further provides "anti-APOA2 protein non-terminus antibodies" that recognize the amino acid sequence of the APOA2 protein excluding its C-terminal region.

The term "anti-APOA2 protein non-terminus antibody" refers to an anti-APOA2 antibody that recognizes and binds to an epitope located in the region in the full-length amino acid sequence of an APOA2 protein variant, excluding the C-terminal region as described above. It means that the anti-APOA2 protein non-terminus antibodies and the anti-APOA2 protein terminus antibodies individually recognize completely different epitopes. The term anti-APOA2 protein non-terminus antibody includes the word "non-terminus antibody" and is conveniently named for the comparison with the anti-APOA2 protein terminus antibody. Thus, antibodies that recognize an epitope not localized in the C-terminal region can be included, without limitation, in the anti-APOA2 protein non-terminus antibodies, even if they recognize and bind to an epitope located at the N-terminus.

The anti-APOA2 protein non-terminus antibodies used in embodiments of the present invention are preferably antibodies which have a nearly equivalent level of binding activity to an APOA2 protein having a certain C-terminal sequence as well as to an APOA2 protein having a different C-terminal sequence and do not prevent the binding of the anti-APOA2 protein terminus antibodies to the C-terminal region. Specifically, for example, the "anti-APOA2-ATQ non-terminus antibody," which binds to the amino acid sequence of the APOA2-ATQ protein represented by SEQ ID NO: 1 excluding its C-terminal region, and the "anti-APOA2-AT non-terminus antibody," which binds to the amino acid sequence of the APOA2-AT protein represented by SEQ ID NO: 2 excluding its C-terminal region, have comparable binding activity to the APOA2 protein and, moreover, either antibody does not prevent the anti-APOA2-ATQ terminus antibody and the anti-APOA2-AT terminus antibody from binding to the C-terminal region of the APOA2 protein. The anti-APOA2 protein non-terminus antibodies may be either polyclonal or monoclonal antibodies, or fragments thereof. Monoclonal antibodies are preferable to enable large-scale production and to achieve a uniform effect.

The term "monoclonal antibody" as used herein refers to an antibody composed of a single immunoglobulin, or an antibody that comprises the framework regions (hereinafter referred to as "FRs") and complementarity determining regions (hereinafter referred to as "CDRs") of an immunoglobulin and can specifically recognize and bind to a particular antigen (epitope).

Each typical immunoglobulin molecule is composed as a tetramer comprising two sets of polypeptide pairs linked by disulfide bonds, each pair consisting of two polypeptide chains called heavy and light chains. A heavy chain is composed of an N-terminal heavy chain variable region (H chain V region: hereinafter referred to as "VH") and a C-terminal heavy chain constant region (H chain C region: hereinafter referred to as "CH"), while a light chain is composed of an N-terminal light chain variable region (L chain V region: hereinafter referred to as "VL") and a C-terminal light chain constant region (L chain C region: hereinafter referred to as "CL"). Among them, VH and VL are particularly important because of their involvement in determining the binding specificity of an antibody. Each of the VH and VL consists of about 110 amino acid residues and has inside three CDRs (CDR1, CDR2, CDR3), which are directly involved in determining the binding specificity to an antigen, and four FRs (FR1, FR2, FR3, FR4), which function as a scaffold for the variable region. It is understood that the CDRs of an antibody form a tertiary structure complementary to an antigen and determine the specificity of the antibody (E. A. Kabat et al., 1991, Sequences of proteins of immunological interest, Vol. 1, 5th ed., NIH publication). The amino acid sequence of the constant region is substantially identical among antibodies from the same species, whereas the amino acid sequences of the CDRs are highly variable among antibodies, thus also called "hypervariable regions". In the variable region, the CDRs and FRs are arranged from N-terminus to C-terminus in the following order: FR1, CDR1, FR2, CDR2, FR3, CDR3, and FR4. In an immunoglobulin molecule, the VL and VH are paired to form a dimer and thereby form an antigen binding site. Immunoglobulin classes of IgG, IgM, IgA, IgE and IgD are known. The antibodies of embodiments of the present invention may be of any of the classes and is preferably of the IgG class.

The anti-APOA2-ATQ terminus monoclonal antibody of embodiments of the present invention specifically binds to the C-terminal region of the APOA2-ATQ protein represented by SEQ ID NO: 1 but not to the APOA2-AT protein represented by SEQ ID NO: 2 and the APOA2-A protein represented by SEQ ID NO: 3. Specific examples of such an antibody include anti-APOA2-ATQ terminus monoclonal antibody clones, for example, as described in Comparative Example 1 below and represented by the antibody clone names 7F2 and 6G2, and the like. The 7F2 clone comprises, in the heavy chain, a CDR1 consisting of the amino acid sequence represented by SEQ ID NO: 4, a CDR2 consisting of the amino acid sequence represented by SEQ ID NO: 5 and a CDR3 consisting of the amino acid sequence represented by SEQ ID NO: 6 and, in the light chain, a CDR1 consisting of the amino acid sequence represented by SEQ ID NO: 7, a CDR2 consisting of the amino acid sequence represented by SEQ ID NO: 8 and a CDR3 consisting of the amino acid sequence represented by SEQ ID NO: 9. Moreover, the 6G2 clone comprises, in the heavy chain, a CDR1 consisting of the amino acid sequence represented by SEQ ID NO: 10, a CDR2 consisting of the amino acid sequence represented by SEQ ID NO: 11 and a CDR3 consisting of the amino acid sequence represented by SEQ ID NO: 12 and, in the light chain, a CDR1 consisting of the amino acid sequence represented by SEQ ID NO: 13, a CDR2 consisting of the amino acid sequence represented by SEQ ID NO: 14 and a CDR3 consisting of the amino acid sequence represented by SEQ ID NO: 15.

The anti-APOA2 protein non-terminus antibodies of embodiments of the present invention are preferably antibodies having the same binding activity to the APOA2 protein variants represented by any of SEQ ID NOs: 1 to 3 when they are compared for the binding activity to the protein variants. Specific examples include anti-APOA2 antibody clones, for example, as represented by the antibody clone names MAB1 and MAB2, and the like. The MAB1 clone comprises, in the heavy chain, a CDR1 consisting of the amino acid sequence represented by SEQ ID NO: 16, a CDR2 consisting of the amino acid sequence represented by SEQ ID NO: 17 and a CDR3 consisting of the amino acid sequence represented by SEQ ID NO: 18 and, in the light chain, a CDR1 consisting of the amino acid sequence represented by SEQ ID NO: 19, a CDR2 consisting of the amino acid sequence represented by SEQ ID NO: 20 and a CDR3 consisting of the amino acid sequence represented by SEQ ID NO: 21. Moreover, the MAB2 clone comprises, in the heavy chain, a CDR1 consisting of the amino acid sequence represented by SEQ ID NO: 22, a CDR2 consisting of the amino acid sequence represented by SEQ ID NO: 23 and a CDR3 consisting of the amino acid sequence represented by SEQ ID NO: 24 and, in the light chain, a CDR1 consisting of the amino acid sequence represented by SEQ ID NO: 25, a CDR2 consisting of the amino acid sequence represented by SEQ ID NO: 26 and a CDR3 consisting of the amino acid sequence represented by SEQ ID NO: 27. Moreover, the above-described anti-APOA2-ATQ non-terminus antibody and the above-described anti-APOA2-AT non-terminus antibody may be used as the anti-APOA2 protein non-terminus antibody.

By the term "a fragment thereof" in the phrase "a polyclonal or monoclonal antibody, or a fragment thereof" is meant a partial fragment (an antibody fragment) of a polyclonal or monoclonal antibody, the fragment forming a polypeptide chain or a complex thereof that has an activity substantially comparable to the antigen-specific binding activity owned by the above antibody. For example, the term refers to an antibody portion containing at least one antigen binding site as described above, namely, a polypeptide chain or a complex thereof having at least one set of VL and VH. Specific examples include a number of well characterized antibody fragments produced by cleavage of immunoglobulins with various peptidases, and the like. More specific examples include Fab, F(ab')$_2$, Fab' and the like. Fab is a fragment generated by cleavage of an IgG molecule with papain at a site N-terminal to the disulfide bonds in the hinge region and each fragment is composed of a polypeptide carrying a VH and a CH1, one of the three domains constituting a CH (CH1, CH2 and CH3) located next to the VH, and a light chain. F(ab')$_2$ is a Fab' dimer generated by cleavage of an IgG molecule at a site C-terminal to the disulfide bonds in the hinge region. Fab' has a structure substantially identical to that of Fab, having a slightly longer H chain than Fab because of the inclusion of the hinge region (Fundamental Immunology (3rd ed.), Paul ed., 1993). Fab' can be obtained by reducing F(ab')$_2$ under mild conditions to cleave the disulfide linkage in the hinge region. Each of these antibody fragments contains an antigen binding site(s) and has an ability to specifically bind to an antigen (that is, in embodiments of the present invention, a certain variant of the APOA2 protein).

The monoclonal antibody fragments of embodiments of the present invention may be fragments synthesized chemically or by using recombinant DNA techniques. Examples include antibody fragments newly synthesized by using recombinant DNA techniques. Specifically, the term refers to, but not limited to, a polypeptide molecule in monomeric form, which is composed of one or more VLs and one or more VHs of a monoclonal antibody of embodiments of the present invention artificially connected with a linker peptide and the like having an appropriate length and sequence, or the polypeptide in multimeric form. Examples of such polypeptides include synthetic antibodies and the like, such as single-chain Fv (ScFv: single chain Fragment of variable region) (see Pierce catalog and Handbook, 1994-1995, Pierce Chemical Co., Rockford, IL), diabody, triabody or tetrabody. In an immunoglobulin molecule, the VL and VH are typically located on separate polypeptide chains (L chain and H chain), whereas a single-chain Fv is a synthetic antibody fragment having a structure with a VL and a VH connected by a flexible linker of sufficient length and thereby including these variable regions in a single polypeptide chain. In a single-chain Fv, both variable regions can undergo self-assembly by mutual association to form one functional antigen binding site. A single-chain Fv can be obtained by expression of a recombinant DNA coding therefor, which has been integrated into the phage genome by using known technologies. Diabody is a molecule having an architecture based on the structure of single-chain Fv in dimeric form (Holliger et al., 1993, Proc. Natl. Acad. Sci. USA, 90: 6444-6448). For example, in cases where the length of the above-described linker is shorter than about 12 amino acid residues, the two variable regions in a single-chain Fv cannot undergo self-assembly but the formation of a diabody, that is, the interaction between two single-chain Fv enables the VL on one Fv chain to assemble with the VH on the other Fv chain, leading to the formation of two functional antigen binding sites (Marvin et al., 2005, Acta Pharmacol. Sin., 26: 649-658). Furthermore, the addition of a cysteine residue to the C-terminus of two single-chain Fvs can result in the formation of a disulfide bond between the Fv chains, leading to the formation of a stable diabody (Alafsen et al., 2004, Prot. Engr. Des. Sel., 17: 21-27). Although diabody is a bivalent antibody fragment as described above, there is no need for each antigen binding site to associate with the same epitope but may have dual specificity that allows each antigen binding site to recognize and specifically bind to a different epitope. Analogously to diabody, triabody and tetrabody have the trimeric and tetrameric structures based on the single-chain Fv structure, respectively, and may be trivalent and tetravalent antibody fragments, respectively, and may be multispecific antibodies. Furthermore, the antibody fragments of embodiments of the present invention include antibody fragments identified using a phage display library (see, for example, McCafferty et al., 1990, Nature, 348: 552-554) and having antigen-binding ability. See also additionally, for example, Kuby, J., Immunology (3rd ed.), 1998, W. H. Freeman & Co., New York.

In embodiments of the present invention, the anti-APOA2 antibodies or fragments thereof may be modified. The modification here includes both functional modification required for the anti-APOA2 antibodies or fragments thereof to have the binding activity specific for the APOA2 protein (for example, glycosylation) and modification for labeling required for the antibodies of embodiments of the present invention or fragments thereof to be detected. Examples of the labeling of antibodies include labeling with a fluorescent dye (FITC, rhodamine, Texas red, Cy3, Cy5), a fluorescent protein (for example, PE, APC, GFP), an enzyme (for example, horseradish peroxidase, alkaline phosphatase, glucose oxidase), or either biotin or (strept)avidin. Moreover, the glycosylation of antibodies may be modified to adjust the affinity of the antibodies for their antigens. Such modification can be achieved by, for example, altering one or more glycosylation sites within the sequence of an antibody. More specifically, for example, one or more amino acid substitutions can be introduced into an amino acid sequence comprising one or more glycosylation sites within FR to remove the above glycosylation sites and consequently eliminate the glycosylation at those sites. Such deglycosylation is effective to increase the affinity of an antibody to its antigen (U.S. Pat. Nos. 5,714,350 and 6,350,861).

1-2. Preparation of Immunogen

In embodiments of the present invention, when an anti-APOA2 protein terminus antibody is produced, an APOA2 protein variant as an immunogen (antigen) is first prepared. Examples of an APOA2 protein variant that can be used as an immunogen in embodiments of the present invention include APOA2 proteins having amino acid sequences shown in any of SEQ ID NOs: 1 to 3 or mutants thereof, or polypeptide fragments of the proteins, or, alternatively, fusion polypeptides between those proteins and other peptides (for example, signal peptide, tag peptide and the like). APOA2 protein variants as immunogens can be synthesized, for example, using the amino acid sequence information of any of SEQ ID NOs: 1 to 3 by a procedure known in the art, such as solid-phase peptide synthesis. For example, the preparation can be performed by the method below.

Any of naturally-occurring APOA2 proteins, recombinant APOA2 proteins, and synthetic APOA2 proteins, whether the whole or a part of each protein is chemically synthesized, can be used as an APOA2 protein variant. For example, with regard to the APOA2 protein variant as an antigen, which is prepared for the obtainment of an antibody that binds to the C-terminus of the APOA2 protein (anti-APOA2 protein terminus antibody), any APOA2 protein-derived variant selected from naturally-occurring APOA2 proteins, recombinant APOA2 proteins, or synthetic APOA2 proteins can be used as long as it comprises an amino acid sequence comprising 6 or more consecutive amino acids of the C-terminal region.

Naturally-occurring APOA2 proteins can be recovered from samples, including body fluid such as blood (including serum and plasma), or cell culture supernatant by using known protein separation and purification techniques, such as gel filtration, ion exchange chromatography, and affinity chromatography.

Recombinant APOA2 proteins can be expressed in microbes, insect cells, or animal cells, into which DNAs encoding the above proteins have been introduced, and then recovered from the above cells using known protein separation and purification techniques.

Synthetic APOA2 proteins can be synthesized, for example, using the published information on the amino acid sequence of the APOA2 protein by a procedure known in the art, such as solid-phase peptide synthesis. These synthetic APOA2 proteins may be linked to a carrier protein such as KLH (keyhole limpet hemocyanin), OVA (ovalbumin), or BSA (bovine serum albumin).

In the production of anti-APOA2 protein terminus antibodies, any fragment selected from fragments of naturally-occurring APOA2 proteins, fragments of recombinant APOA2 proteins, or fragments of synthetic APOA2 proteins may likewise be used when a fragment of an APOA2 protein variant is used as an immunogen. For example, with regard to the APOA2 protein fragment, an oligopeptide or polypeptide comprising 6 or more, preferably 10 or more, preferably 18 or more, more preferably 30 or more, consecutive amino acid residues including the C-terminus in the amino acid sequence represented by any of SEQ ID NOs: 1 to 3 can be used as an antigen. For example, a peptide comprising the amino acid sequence represented by SEQ ID NO: 28 or 29 can be used.

In cases where a fragment of a naturally-occurring APOA2 protein is used as an immunogen, for example, to produce an anti-APOA2 protein terminus antibody, purified APOA2 proteins are first treated with an appropriate protease, such as trypsin, and then applied to a reverse-phase column for the separation and collection of peaks. Subsequently, the amino acid sequence of a peptide corresponding to each peak is identified with a mass spectrometer. One of the peptides may be used as an immunogen if the peptide comprises a sequence comprising, as a partial sequence, 6 or more consecutive amino acids in the C-terminal region of the APOA2 protein represented by any of SEQ ID NOs: 1 to 3.

In cases where a partial amino acid sequence of a recombinant APOA2 protein is used as an immunogen, for example, to produce an anti-APOA2 protein terminus antibody, a DNA sequence coding for a peptide in the APOA2 protein represented by any of SEQ ID NOs: 1 to 3 is first inserted into an expression vector, which peptide consists of a partial sequence comprising 6 or more consecutive amino acids including the C-terminal amino acid residue (C-terminal fragment). Subsequently, the expression vector is introduced into various cells for the expression of the encoded C-terminal fragment. Finally, the C-terminal fragment is extracted from the cells according to routine procedures after the completion of the expression. The obtained C-terminal fragment may be used as an immunogen.

In embodiments of the present invention, moreover, also in cases where an anti-APOA2 protein non-terminus antibody is produced, the basic preparation method may be identical to the above-described production method for anti-APOA2 protein terminus antibodies. However, with regard to the region in the APOA2 protein available as an immunogen, a region different from those employed in the production of anti-APOA2 protein terminus antibodies is used. It means that the whole or a part of the region of the APOA2 protein, excluding the C-terminal region, may be used as an immunogen. Similarly to the production of anti-APOA2 protein terminus antibodies, also in cases where an anti-APOA2 protein non-terminus antibody is produced, an oligopeptide or polypeptide comprising amino acid residues in the region of the APOA2 protein, excluding the C-terminal region, can be used as an antigen.

(Preparation of Recombinant APOA2 Proteins)

The preparation of recombinant APOA2 proteins represented by any of SEQ ID NOs: 1 to 3 (recombinant APOA2 protein variants) will be described in detail below.

(a) Preparation of a Polynucleotide Encoding a Recombinant APOA2 Protein Variant Phages or plasmids capable of autonomous replication in host microbes can be used as vectors for use in the expression of various APOA2 protein variants. Examples of the plasmids include plasmids derived from *E. coli* (pET30a, pGEX6p, pUC118, pUC119, pUC18, pUC19 and the like), plasmids derived from Bacillus subtilis (pUB110, pTP5 and the like), plasmids derived from yeasts (YEp13, YEp24, YCp50 and the like), and the like. Moreover, examples of the phages include λphages (λgt11, λZAP and the like).

Furthermore, vectors of animal viruses such as vaccinia virus or insect viruses such as baculovirus may also be used.

Examples of a method for inserting a polynucleotide encoding an APOA2 protein variant into the above-described vector include a method involving the cleavage of the above polynucleotide after purification with an appropriate restriction enzyme(s), followed by the ligation of the resulting polynucleotide using DNA ligase and the like into a vector cleaved with the corresponding appropriate restriction enzyme(s).

(b) Introduction of the APOA2 Protein Variant-Expressing Vector into a Host

Transformants capable of the expression of the APOA2 protein variant (variant-expressing transformants) are obtained by introducing the obtained APOA2 protein variant-expressing vector into a host in which expression from the expression vector is successfully accomplished. The used host is a host suitable for the used vector but is not particularly limited as long as it can allow APOA2 protein variants to be expressed. For example, bacteria (colibacillus (for example, *Escherichia coli*), hay bacillus (for example, Bacillus subtilis) and the like), yeasts, insect cells, animal cells (COS cells, CHO cells (Journal of Immunology, 1998, 160: 3393-3402)) and the like are preferably used. The method to introduce the above-described vectors to the bacteria is not particularly limited as long as the method is a known method for introducing the above vectors into the bacteria. Examples of the method include the heat shock method, a method using calcium ions, electroporation and the like. All of these techniques are known in the art and have been described in various literature. See, for example, Green & Sambrook, 2012, Molecular Cloning: A Laboratory Manual (4th ed.), Cold Spring Harbor Laboratory Press, Cold Spring Harbor, N.Y. Moreover, for the transformation of animal cells, the lipofectin method (PNAS, 1989, 86: 6077; PNAS, 1987, 84: 7413), electroporation, the calcium phosphate method (Virology, 1973, 52: 456-467), the DEAE-dextran method and the like are preferably used.

In cases where a bacterium is used as a host, preferably, the APOA2 protein variant-expressing vector is capable of autonomous replication in the above bacterium and, at the same time, comprises a promoter sequence, a ribosome-binding sequence, an APOA2 protein variant-coding DNA sequence and a transcription termination sequence. Moreover, the expression vector may comprise a gene coding for a regulator that controls the promoter. Any promoter may be used as long as it is functional in a host such as *E. coli*.

Also in cases where a eukaryotic cell, such as yeast, animal cells, insect cells and the like, is used as a host, APOA2 protein variant-expressing transformants can likewise be obtained by following a procedure known in the art. The APOA2 protein variant-expressing vector used in eukaryotic cells may be linked with, in addition to a promoter sequence and an APOA2 protein variant-coding DNA sequence, a cis-element such as enhancer, splicing signals (signals for donor site, acceptor site, branch point and the like), a polyadenylation signal, a selection marker sequence, a ribosome-binding sequence (SD sequence) and the like, as required.

(c) Culture of the Variant-Expressing Transformant and Expression of the Recombinant APOA2 Protein Variant Subsequently, the variant-expressing transformant produced above is cultured. The method to culture the variant-expressing transformant is carried out according to a culture method conventionally used for the host. For example, in cases where a bacterium is used as a host, the type of culture medium is not particularly limited as long as the medium contains a carbon source, nitrogen source, inorganic salts and the like, which can be assimilated by the bacterium, and allows the bacterium to grow and proliferate. Either a natural or synthetic medium can be used. More specific examples include, but of course not limited to, the LB medium. Moreover, for the selective culture of the variant-expressing transformant, an antibiotic such as ampicillin or tetracycline may be added as necessary to the culture medium. The culture is usually maintained at 37° C. for 6 to 24 hours under aerobic conditions, for example, with continuous aeration and stirring. During the culture period, the pH is preferably maintained around neutral. The pH is adjusted with an inorganic or organic acid solution, an alkaline solution and the like. In cases where the variant-expressing transformant is based on animal cells such as CHO cell, the host cells may be inoculated in DMEM medium manufactured by Life Technologies, LLC. (currently known as Thermo Fisher Scientific, Inc.) to a density of $1 \times 10^5$ cells/ mL and cultured in an incubator at 37° C. and 5% $CO_2$. During the culture, an antibiotic such as ampicillin or tetracycline may be added as necessary to the culture medium.

In cases where the above-described APOA2 protein variant-expressing vectors are in the form of an inducible protein expression vector comprising a regulatory system for protein expression (corresponding to, in the case of a bacterial host, a repressor gene, an operator and the like, for example), a predetermined treatment should be performed on the variant-expressing transformants to induce the expression of the APOA2 protein variant. Since the method to induce the expression is different depending on the regulatory system for protein expression contained in each vector, an induction treatment suitable for each system may be performed. For example, a system comprising the lac repressor gene and the lac operator is the regulatory system for protein expression most commonly used in inducible protein expression vectors for bacterial hosts. With this system, expression can be induced by the treatment with IPTG (isopropyl-1-tio-β-D-galactoside). In transformants harboring an APOA2 protein expression vector that comprises this system, it is sufficient for the expression of a protein of interest, the APOA2 protein variant, to add an adequate amount of IPTG (for example, a final concentration of 1 mM) to the culture medium.

(d) Extraction and/or Recovery of the Recombinant APOA2 Protein Variant

In cases where the APOA2 protein variant is produced and stored in bacterial bodies or cells, the protein of interest can be extracted by recovering and breaking the bacterial bodies or cells after the completion of the culture. Moreover, in cases where the APOA2 protein variant is secreted outside of bacterial bodies or cells, the culture liquid may be used directly, or the supernatant may be used after the removal of the bacterial bodies or the cells by centrifugation and the like. Subsequently, the APOA2 protein variant can be isolated and purified from the culture using conventional protein purification methods, either individually or in appropriate combinations, such as ammonium sulfate precipitation, gel filtration, ion exchange chromatography, affinity chromatography and the like. It may be confirmed by SDS-polyacrylamide gel electrophoresis and the like whether or not the APOA2 protein variant has been obtained.

1-3. Production of Anti-APOA2 Monoclonal Antibodies
1-3-1. Production Methods for Anti-APOA2 Monoclonal Antibodies and Hybridomas Hybridomas that produce anti-APOA2 monoclonal antibodies of embodiments of the present invention can be produced by the method described below. However, the production method is not limited to that method and they can also be produced by any other methods known in the art.

(1) Production Method for Anti-APOA2 Monoclonal Antibodies

For the purpose of producing anti-APOA2 protein terminus monoclonal antibodies that specifically bind to, among other amino acid sequences constituting APOA2 proteins, the C-terminal region of any APOA2 protein represented by SEQ ID NO: 1, 2 or 3, monoclonal antibodies may be produced to an APOA2 protein variant or a peptide comprising the C-terminal region of an APOA2 protein variant as an immunogen and then screened using an intact APOA2 protein represented by any of SEQ ID NOs: 1 to 3 or the peptide comprising the C-terminal region of the APOA2 protein variant for an antibody that binds to a particular APOA2 protein variant alone. For example, an anti-APOA2-ATQ terminus monoclonal antibody can be screened on the basis of specific binding to the C-terminal region of the APOA2-ATQ protein represented by SEQ ID NO: 1 and no or little binding to the APOA2 protein variant represented by SEQ ID NO: 2 or 3. Moreover, an anti-APOA2-AT terminus monoclonal antibody can be screened on the basis of specific binding to the C-terminal region of the APOA2-AT protein represented by SEQ ID NO: 2 and no or little binding to the APOA2 protein variant represented by SEQ ID NO: 1 or 3.

Moreover, for the purpose of producing anti-APOA2 protein non-terminus antibodies that recognize the amino acids of the APOA2 protein excluding the C-terminal region, monoclonal antibodies can be produced to an APOA2 protein variant or a peptide comprising a partial sequence thereof as an immunogen and then screened on the basis of a similar level of binding activity when compared among the binding activity to the APOA2 protein variants represented by any of SEQ ID NOs: 1 to 3 or to peptides thereof having a different C-terminus, and thereby the desired antibodies can be obtained.

(2) Production of Anti-APOA2 Antibody-Producing Cells

A recombinant APOA2 protein, which is an immunogen obtained according to the above section 1-2, is dissolved in a buffer to prepare an immunogen solution. On this occasion, an adjuvant may be added, if necessary, to the buffer for effective immunization. Examples of the adjuvant include commercially available Freund's complete adjuvant (FCA), Freund's incomplete adjuvant (FIA) and the like. These adjuvants may be used individually or in combination.

Next, the prepared immunogen solution is administered to a mammal, such as rat, mouse (for example, BALB/c inbred mouse), rabbit and the like, for immunization. Examples of a method for administrating the immunogen include, but not limited to, subcutaneous injection using FIA or FCA, intraperitoneal injection using FIA, or intravenous injection using 0.15 moles of sodium chloride. A single dose of the immunogen is appropriately determined depending on the species of an animal to be immunized, administration route and the like and is in the range of about 50 to 200 μm per animal. Moreover, the interval between immunizations is not particularly limited, but booster immunization is given 2 to 6 times, preferably 3 to 4 times, with an interval of several days to several weeks, preferably 1 to 4 weeks, after the initial immunization. From the initial immunization, the immunized animal will be measured for the antibody titer in serum by ELISA (Enzyme-Linked Immunosorbent Assay). Upon the indication of an adequate increase in antibody titer, the immunogen is injected intravenously or intraperitoneally as a final immunization. Subsequently, antibody-producing cells are collected 2 to 5 days, preferably 3 days, after the final immunization.

1-3-2. Production Method for Hybridomas Producing Anti-APOA2 Monoclonal Antibodies (1) Recovery of Antibody-Producing Cells from Immunized Animals and Cell Fusion Hybridomas producing monoclonal antibodies that specifically recognize particular regions of the APOA2 protein can be produced through the cell fusion between antibody-producing cells obtained from the immunized animals and myeloma cells. Examples of the antibody-producing cells include spleen cells, lymph node cells, peripheral blood cells and the like, and spleen cells or local lymph node cells are preferable. Cells of a commonly available established cell line derived from mouse or the like can be used as myeloma cells to be fused with antibody-producing cells. The cell line to be used preferably has the following characteristics: being selectable by a drug, inviable in an unfused form in the HAT selection medium (containing hypoxanthine, aminopterin and thymine), and viable only in a fused form with antibody-producing cell in the same medium. Moreover, the established cell line is preferably derived from the same species or strain of animals as the immunized animals. Specific examples of myeloma cells include cells of cell lines derived from BALB/c mouse and deficient in hypoxanthine guanine phosphoribosyltransferase (HGPRT), such as the strain P3X62-Ag.8 (ATCC TIB9), P3X63-Ag.8.U1 (JCRB9085), P3/NS1/1-Ag4-1 (JCRB0009), P3x63Ag8.653 (JCRB0028), or SP2/0-Ag14 (JCRB0029).

For the cell fusion between the above-described myeloma cells and antibody-producing cells, in a serum-free medium for animal cell culture, such as the DMEM or RPMI 1640 medium, the antibody-producing cells and the myeloma cells are mixed at a ratio of about 1:1 to 20:1 and undergo a fusion reaction in the presence of a cell fusion promoter. Polyethylene glycol having an average molecular weight of 1,500 to 4,000 Da and the like can be used as a cell fusion promoter at a concentration of about 10 to 80%. Moreover, if necessary, an auxiliary agent such as dimethyl sulfoxide may be used in combination therewith to increase the efficiency of fusion. Furthermore, the antibody-producing cells and the myeloma cells can also be fused with each other using a commercially available cell fusion apparatus that employs electric stimulation (for example, electroporation) (Nature, 1977, 266: 550-552).

(2) Selection of Hybridomas of Interest

Examples of a method for selecting hybridomas that produce the anti-APOA2 monoclonal antibodies of interest from the cells after the cell fusion process include the method below. The cell suspension is diluted with, for example, the RPMI 1640 medium and the like containing fetal bovine serum and then seeded at approximately $2 \times 10^6$ cells/well in 96-well microtiter plates. Then, a selection medium is added to each well and the culture is maintained hereafter by changing the selection medium as necessary. The culture temperature will be a temperature of 20 to 40° C., preferably about 37° C. In cases where the myeloma cells are of a HGPRT-deficient or thymidine kinase (TK)-deficient line, the use of the selection medium containing hypoxanthine, aminopterin and thymidine (HAT medium) can selectively allow hybridomas between the antibody-producing cells and the myeloma cells to grow and proliferate. Therefore, cells that have started their growth on the selection medium from approximately 10 days after the initiation of culture may be selected as hybridomas.

The hybridomas selected with the HAT medium are first screened for produced antibodies based on the binding activity to various APOA2 protein variants represented by any of SEQ ID NOs: 1 to 3. Next, the cross-reactivity is examined in antibodies that have binding activity to the variants, and acceptable ones are chosen. The term "acceptable ones (in cross-reactivity)" means a negligible level of cross-reactivity in applications of the antibodies of interest. For example, in the case of a monoclonal antibody for use in immunological measurement, the monoclonal antibody is considered to undergo practically no cross-reaction when the signal intensity for the cross reaction is kept in the range from the background level to a level of less than 1% of the signal intensity arising from a specific reaction.

The reaction specificity for a particular APOA2 protein variant can be confirmed, for example, using ELISA. In ELISA, various APOA2 protein variants or fragments thereof are provided as antigens individually immobilized on different wells of a microplate and are allowed to react by addition of samples of appropriately diluted culture supernatants of the above-described hybridomas. After sufficient reaction, the wells are washed and further allowed to react by addition of a labeled secondary antibody against an immunoglobulin. The wells are washed again and then assayed using the label of the secondary antibodies remaining bound to the wells. Thus, the binding activity of an antibody present in each culture supernatant can be quantitatively defined for each antigen. For example, in the production of anti-APOA2 protein terminus monoclonal antibodies, the specificity should be defined based on the indication that the binding activity is shown for the C-terminal region of a particular APOA2 protein variant alone and no cross-reactivity is shown for other APOA2 protein variants. Alternatively, in the production of anti-APOA2 protein non-terminus monoclonal antibodies, antibodies should be selected based on the indication that a similar level of binding activity is shown for any APOA2 protein variants having different C-termini and that the binding of anti-APOA2 protein terminus monoclonal antibodies to the C-terminal region is not prevented by the produced antibodies.

Hybridomas can also be selected using recombinant DNA techniques. First, mRNA is extracted from a population of hybridomas obtained according to the aforementioned method. A method known in the art may be used for the extraction of mRNA. Subsequently, cDNA copies are obtained from the mRNA using an oligo-dT primer or random primer. PCR is performed using the cDNA as a template and a set of primers, one comprising the base sequence of the signal sequence upstream of a variable region-coding gene and the other comprising a base sequence on the constant region side. Cloning of the obtained amplicons in an appropriate cloning vector can yield a library of the variable region genes of the antibodies produced by the hybridomas. By way of a more specific example, without limitation, PCR is performed using Mouse Ig Primers provided by Merck Millipore KGaA and the amplicons (cDNA copies of mouse immunoglobulin variable region) are inserted for cloning to the Eco RI site of Zero Blunt PCR Topo Vector provided by Life Technologies, LLC. (currently known as Thermo Fisher Scientific, Inc.) and a collection of the obtained vectors can be used as a library of genes coding for the amino acid sequences of variable regions. Next, probes are designed based on the amino acid sequences of the variable regions or CDRs disclosed in the present invention and the above-described library is screened for positive clones with those probes.

Thus, hybridomas that produce antibodies of embodiments of the present invention can be selected.

(3) Use of Hybridomas for Antibody Production

The hybridomas according to embodiments of the present invention can be used for antibody production by ascites induction in mouse. Specifically, mice from which originated the cells as a fusion partner used in the production of the hybridomas, or nude mice are inoculated intraperitoneally with the hybridomas and ascites fluid is collected appropriately and, consequently, the ascites fluid containing antibodies can be harvested. More specifically, BALB/c mice are inoculated intraperitoneally with pristane and 10 days later with the hybridomas developed by using SP2/0 cells as a fusion partner and, consequently, the ascites fluid containing antibodies can be harvested.

Moreover, the hybridomas according to embodiments of the present invention can be used for antibody production, in which a suitable culture medium is used for the culture of the hybridomas. Specifically, without limitation, the hybridomas are inoculation in the Hybridoma-SFM medium manufactured by Life Technologies, LLC. (currently known as Thermo Fisher Scientific, Inc.) to a density of $1 \times 10^5$ cells/mL and cultured in an incubator at 37° C. and 5% $CO_2$ until the hybridomas are killed and, consequently, culture supernatants containing antibodies can be obtained.

(4) Method for Producing Recombinant Anti-APOA2 Monoclonal Antibodies or Fragments Thereof by Recombinant DNA Procedures The antibodies of embodiments of the present invention or fragments thereof can also be obtained by recombinant DNA procedures using the cDNA sequences coding for the amino acid sequences of those antibodies.

The use of base sequences coding for the amino acid sequences of the variable regions in an antibody derived from an anti-APOA2 monoclonal antibody-producing hybridoma, such as antibodies derived from an anti-APOA2 protein terminus monoclonal antibody-producing hybridoma obtained by the above method described in the section "1-3-2(2)," can allow the base sequences of the VH and VL to be linked with the base sequences encoding any human CL and human CH, respectively, and each of the resulting polynucleotides to be integrated into an appropriate expression vector, introduced into a host cell(s), and then expressed as an intact immunoglobulin molecule. Alternatively, the use of the CDR grafting antibody technique may allow polynucleotides encoding the amino acid sequences of the CDR sequences within the amino acid sequences of the variable regions in an antibody, which is derived from an anti-APOA2 protein terminus monoclonal antibody-producing hybridoma obtained by the above method described in the section "1-3-2(2)," to be connected with polynucleotides encoding the amino acid sequences of human FR sequences in a given order, and each of the resulting polynucleotides to be integrated into an appropriate expression vector, introduced into a host cell(s), and then expressed as an intact immunoglobulin molecule. It is convenient for this process to express heavy and light chains in the same host cell and to produce a dimer composed of the heavy and light chains. Specifically, for example, cells can be co-transformed with a light chain expression vector and a heavy chain expression vector to obtain an antibody according to embodiments of the present invention from those transformed cells. Alternatively, each of the polynucleotides encoding the amino acid sequences of the above-described variable regions can also be directly integrated into an appropriate expression vector, introduced into host cells, and then expressed as fragments of an immunoglobulin molecule. Alternatively, as described above, polynucleotides encoding the VL and VH, or the light chain and heavy chain, comprising the above-described amino acid sequences may be connected via an appropriate linker, integrated in the phage, and then expressed as a single-chain Fv or a synthetic antibody fragment such as diabody. In addition, according to the recently developed phage display antibody technique (Brinkmann et al., 1995, J. Immunol. Methods, 182, 41-50; International Publication Nos. WO97/13844 and WO90/02809), which utilizes genetic engineering techniques to express recombinant antibodies on phage surface, diverse single-chain Fv antibodies resulted from artificial shuffling of genes encoding heavy and light chains are expressed as phage fusion proteins and thereby specific antibodies can be obtained.

The preparation of a polynucleotide encoding a recombinant anti-APOA2 antibody or a fragment thereof, the preparation of a vector integrated with the polynucleotide and the introduction of the vector to a host may be carried out using recombinant DNA techniques known in the art. The recombinant anti-APOA2 protein antibody of interest or a fragment thereof can be obtained from the culture media of the transformed cells or from the inside of those cells.

By way of examples of an immunoglobulin expression vectors, plasmids, phagemids, cosmids, virus vectors (for example, SV40 virus-based vectors, EB virus-based vectors, BPV-based vectors) and the like can be used, but not limited thereto. For example, the BCMGS Neo vector, one of the BPV-based vectors, is a desirable vector that efficiently expresses a foreign gene in COS7 cells and the like upon transformation (Hajime Karasuyama, "Bovine papilloma virus vectors" in Masami Muramatsu and Hiroto Okayama eds., 1991, Experimental Medicine Supplement: Genetic Engineering Handbook, Yodosha Co., Ltd., 297-299).

Each of the above-described vectors can harbor, in addition to a polynucleotide encoding an antibody or a fragment thereof, regulatory elements essential for the expression of the antibody or a fragment thereof (for example, a promoter, an enhancer, a terminator, a polyadenylation site, splicing sites), or, if necessary, a selection marker.

As a host for transformation, in addition to the hosts described above in the section "1-2. Preparation of immunogen," the SP2/0 (mouse myeloma) cell (European Journal of Cancer Research Prevention (1996) 5: 512-519: Cancer Research (1990) 50: 1495-1502) is preferably used.

In host cells according to embodiments of the present invention which harbor a vector that expresses an antibody or a fragment thereof, the antibody can be produced in the culture supernatant or in the host cells by culturing the host cells according to a conventional method. Specifically, in cases where CHO cell is used as a host, the host cells are inoculated in the DMEM medium manufactured by Life Technologies, LLC. (currently known as Thermo Fisher Scientific, Inc.) to a density of $1 \times 10^5$ cells/mL and cultured in an incubator at 37° C. and 5% $CO_2$ and, consequently, a culture supernatant containing antibodies can be obtained. Alternatively, for example, in cases where the host cell is *E. coli*, the host is inoculated in a culture medium commonly used for the culture of *E. coli*, such as the LB medium, cultured and induced for protein expression and, consequently, the antibody can be produced in the culture supernatant or in the host cells.

When the expression product, namely an antibody or a fragment thereof, contains a constant region, the product can be recovered and purified from the culture supernatant or cell lysate by using Protein A column, Protein G column, anti-immunoglobulin antibody affinity column and the like. On the other hand, when the product is composed of a variable region alone and expressed in a form without constant regions, other suitable purification methods are employed because the above-described method is not applicable. For example, if the product is expressed as a fusion with a C-terminal tag sequence advantageous for purification, such as histidine tags, the product can be purified by affinity chromatography using the corresponding ligand. In cases where the product is not a tagged fusion protein, the product can be purified according to conventional methods for protein purification including ammonium sulfate precipitation, ion exchange chromatography, reverse-phase chromatography, gel filtration chromatography, and hydroxyapatite chromatography.

Additionally, the monoclonal antibodies used in embodiments of the present invention or fragments thereof are preferably examined for cross-reactivity with other variants in advance of use, as mentioned above, to confirm their specificity for a particular APOA2 protein variant or a fragment thereof. For example, in the anti-APOA2-ATQ protein terminus monoclonal antibody of embodiments of the present invention or a fragment thereof, antigens to be examined for cross-reactivity are the APOA2-AT protein and the APOA2-A protein.

Moreover, the antibodies used in embodiments of the present invention or fragments thereof are more preferably examined for cross-reactivity with, in addition to the above-described proteins, other proteins that have a partial structure shared with the APOA2 protein variants. For example, ELISA using the APOA2-ATQ protein as an antigen can be employed to check the cross reaction. When another antigen protein to be examined for its cross-reactivity coexists in the reaction of an antibody to be examined for its reaction specificity, namely an anti-APOA2 terminus antibody and a fragment thereof, with the APOA2 protein variant, the cross-reactivity can be examined by observing the competition between both antigens. In such a method to examine cross-reactivity based on the principle of competitive inhibition, a reaction system is not required to be prepared for each antigen and, thus, the screening can be carried out quickly.

1-3-3. Examination on the Regional Structure in the APOA2 Protein Recognized by the Obtained Anti-APOA2 Protein Terminus Monoclonal Antibodies The types of the APOA2 protein variants specifically recognized by the obtained anti-APOA2 monoclonal antibodies can be determined by preparing gene of various APOA2 protein variants by PCR and the like based on the gene of the above protein and then analyzing the binding activity of the monoclonal antibodies to the various APOA2 protein variants derived from the above genes.

In the case of the anti-APOA2 protein terminus monoclonal antibodies, specifically, the method as described below is carried out. First, the full-length APOA2 gene or various lengths of fragments representing the APOA2 gene with deletion of 6 or 9 bases, including the stop codon, from the stop codon to the 5'-end is prepared and expression vectors inserted with these fragments are produced. Such a method for preparing gene fragments carrying deletion mutations is described in "Zoku-Seikagaku Jikken Koza, Vol. 1: Idenshi Kenkyu-hou II (Biochemical Experiment Training Course, Sequel series, Vol. 1: Methods in gene research II), The Japanese Biochemical Society, ed., pp.289-305." Next, various APOA2 protein variants are prepared by the aforementioned method from host cells into which each APOA2 protein variant-expressing vector has been introduced. Subsequently, these proteins are used as antigens in ELISA, in which the binding activity of anti-APOA2 protein monoclonal antibodies to those various APOA2 protein variants is evaluated. When the binding activity is shown for a particular variant but no or little binding activity is shown for other variants, the monoclonal antibody may be determined as an anti-terminus monoclonal antibody that specifically binds to the particular APOA2 protein variant alone.

APOA2 protein variants recognized by the obtained anti-APOA2 protein terminus monoclonal antibodies can also be identified by a method as described below.

First, peptides having the sequences corresponding to the C-terminal regions of various APOA2 protein variants are solid-phase synthesized by a known method. Subsequently, these peptides are used as antigens in ELISA, in which the binding activity of anti-APOA2 protein terminus monoclonal antibodies to those various peptides is evaluated. When the binding activity of an anti-APOA2 protein monoclonal antibody is shown for a peptide having a sequence corresponding to a particular C-terminal region but no or little binding activity is shown for other variants, the monoclonal antibody may be determined as an anti-APOA2 protein terminus monoclonal antibody that specifically binds to the particular APOA2 protein variant.

1-4. Production of Anti-APOA2 Polyclonal Antibodies

An anti-APOA2 polyclonal antibody can be produced by a method known in the art. By way of an example, a method for obtaining an anti-APOA2 protein terminus antibody that specifically binds to a particular APOA2 protein variant alone will be specifically indicated below.

1-4-1. Obtainment of Antiserum

The production of an anti-APOA2 protein terminus polyclonal antibody may be carried out similarly to the production method described in the section 1-3-1(2) for anti-APOA2 antibody-producing cells. An antigen to be used may be a C-terminal fragment with a length of at least 6 amino acids or more from the sequence of a particular APOA2 protein variant, such as the peptide represented by SEQ ID NO: 28 or 29. An antiserum containing a polyclonal antibody that recognizes the APOA2 protein can be harvested from the blood of an immunized animal 2 to 5 days, preferably 3 days, after the final immunization.

1-4-2. Purification of Anti-APOA2 Antibodies (1) Production of Peptide-Immobilized Column Affinity columns are produced, on which either a peptide corresponding to the C-terminal region of the APOA2 protein or a peptide corresponding to the C-terminal region of the APOA2 protein and modified by the addition of an amide group to the C terminus is immobilized. The detailed method is described in "Experimental Protocols for Anti-Peptide Antibodies," 2nd ed., Gakken Medical Shunjunsha Co., Ltd. Examples of carriers used in the affinity columns include carriers, such as formyl-Cellulofine and CNBr agarose, which have functional groups capable of binding to amino groups of peptides, or carriers capable of binding to cysteine residues of peptides in their sequences through the interaction with maleimide groups covalently linked to the carriers, or the like. Moreover, the length of the peptides to be immobilized is 6 or more amino acids, preferably 10 or more amino acids, preferably 18 or more amino acids, and more preferably 30 or more amino acids, as long as those peptide contains the C-terminus of the APOA2 protein.

(2) Purification of Antibody

An anti-APOA2 protein terminus polyclonal antibody can be purified using the peptide-immobilized affinity columns from the above-described antiserum. For example, the antiserum is diluted with a suitable buffer, IgG antibodies contained in the diluted antiserum are allowed to be adsorbed to the affinity column containing the immobilized peptide which corresponds to the C-terminal region of the APOA2 protein, and then the adsorbed fraction is recovered. Subsequently, the affinity column containing the immobilized C-terminally amidated peptide of the APOA2 protein is used to remove immunoglobulins which have binding activity to the peptide excluding the C-terminal region through their adsorption onto the column. Finally, the unadsorbed fraction is obtained as an anti-APOA2 protein terminus polyclonal antibody that specifically recognizes a particular APOA2 protein variant.

2. Detection Method for Biliary Tract Cancer

The second aspect of embodiments of the present invention relates to a method for assisting diagnosis characterized by detection of biliary tract cancer in vitro. An embodiment of the present invention is that anti-terminus antibodies (anti-APOA2 protein terminus antibodies) or fragments thereof, which specifically recognize the C-terminal region of either of two APOA2 protein variants, namely, the APOA2-ATQ protein and the APOA2-AT protein, and anti-APOA2 protein antibodies (anti-APOA2 protein non-terminus antibodies) or fragments thereof, which recognize the amino acid sequences corresponding to their regions, excluding their C-terminal regions, are used to measure the two APOA2 protein variants. A further embodiment of the present invention is a method for detecting biliary tract cancer through a multivariate analysis using the measured values of the quantified two APOA2 protein variants.

Embodiments of the method of the present invention comprises a process of measuring markers for the detection of biliary tract cancer and a determining process. Those processes are described in detail below.

2-1. Process of Measuring Markers for the Detection of Biliary Tract Cancer

The "process of measuring markers for the detection of biliary tract cancer" is a process of measuring in vitro the quantity of markers for the detection of biliary tract cancer, namely the amounts of two APOA2 protein variants consisting of the APOA2-ATQ protein and the APOA2-AT protein, present in a body fluid derived from a test subject.

In this specification, the term "test subject" refers to an individual as a target for the detection of biliary tract cancer, preferably an individual suspected of having biliary tract cancer. Examples of the individual here include vertebrates. It is preferably a mammal, for example, a primate (human, monkey, chimpanzee, orangutan, gorilla and the like), a rodent (mouse, rat, guinea pig and the like), a ungulate (cow, horse, sheep, goat and the like) and the like, and more preferably human. In this specification, when a test subject is a human, hereinafter, the test subject is specially referred to as "subject".

In this specification, the term "body fluid" refers to a sample provided for the detection of biliary tract cancer and means biological fluid. The body fluid is not particularly limited but may be a biological fluid that potentially contains the markers of the present invention for detecting biliary tract cancer. Examples of the body fluid include blood, urine, lymphocyte culture supernatant, cerebrospinal fluid, digestive fluid (including, for example, pancreatic fluid, colon fluid, fluids secreted from the esophageal gland, and saliva), sweat, ascites, nasal mucus, tear fluid, vaginal secretion, semen and the like. It is preferably blood or urine. In this specification, the term "blood" includes plasma and serum, and whole blood may preferably be used. The type of whole blood is not limited, but includes venous blood, arterial blood, cord blood and the like. The body fluid may be a combination of two or more different fluids obtainable from the same individual. Embodiments of the method of the present invention for detecting biliary tract cancer permits the detection even in a low invasive blood or urine sample and, therefore, considered to be very useful as a convenient detection method.

The phrase "body fluid derived from a test subject" refers to a body fluid which has already been collected from a test subject. The act of collecting body fluid per se is not included in an aspect of the present invention. A body fluid derived from a test subject may be applied to embodiments of the method of the present invention immediately after the collection from the test subject. Alternatively, the body fluid refrigerated or frozen after the collection, directly or with an appropriate treatment, may be brought back to room temperature before application and then applied to embodiments of the method of the present invention. The appropriate treatment before refrigeration or freezing include, in cases where the body fluid is blood, anticoagulation treatment by the addition of heparin and the like to the collected whole blood, followed by separation into plasma or serum, and the like. These treatments may be performed based on techniques known in the art.

In this specification, the phrase "the amounts of APOA2 protein variants" refers to the quantity of either of the above-described two APOA2 protein variants present in a body fluid derived from a test subject. The quantity may be an absolute or relative amount. When the quantity represents an absolute amount, it corresponds to the mass or capacity of either of the two APOA2 protein variants contained in a given volume of body fluid. When the quantity represents a relative amount, it refers to, for example based on the use of a standard reference substance, a relative value determined by comparing the measured value of either of the two APOA2 variants derived from a test subject to the measured value of the standard reference substance. Examples of the relative amount include concentration, fluorescence intensity, absorbance and the like.

The amounts of the APOA2 protein variants can be measured in vitro using a known method. Examples of the method include a method in which substances capable of specific binding to either of the two APOA2 protein variants are used for measurement.

In this specification, the phrase "capable of specific binding to" means that a certain substance can substantially bind to a particular APOA2 protein variant, that is, a target of the present invention alone. In this case, non-specific binding may be present at such a level that the detection of a particular APOA2 protein variant is not influenced.

Examples of "the substances capable of specific binding" include APOA2 binding proteins. More specifically, the substances capable of specific binding are, for example, "anti-APOA2 protein terminus antibodies" raised against APOA2 protein variants as antigens and recognizing the difference in structure among the C-terminal regions of and binding to the APOA2 protein variants, preferably "anti-human APOA2 protein terminus antibodies" each raised against a human APOA2 protein variant comprising the amino acid sequence of SEQ ID NO: 1, 2 or 3 as an antigen and recognizing and binding to any one of the APOA2 protein variants alone, or antibody fragments thereof. Alternatively, the substances capable of specific binding may be chemically modified derivatives thereof. The "chemically modified derivatives" here include, for example, both functional modification required for the above anti-APOA2 protein terminus antibodies or antibody fragments thereof to acquire or retain the binding activity specific for a particular APOA2 protein variant and modification for labeling required for the above anti-APOA2 protein terminus antibodies or antibody fragments thereof to be detected. The functional modification is as described above.

The antibody used for the detection of the APOA2 protein variants may be either polyclonal or monoclonal antibody. Monoclonal antibody is preferable to allow specific detection. For example, an anti-APOA2 protein terminus polyclonal antibody and the like that specifically bind to the APOA2 protein terminus can be produced by the aforementioned method.

The two APOA2 protein variants can be measured by an immunological method using anti-APOA2 antibodies individually binding to a particular APOA2 protein variant alone. The immunological method may be any method as long as anti-APOA2 antibodies are used, and it is preferably ELISA which is performed using anti-APOA2 protein terminus antibodies as immobilized or labeled antibodies in combination with another antibody which binds to the region of the APOA2 protein, excluding the C-terminus (anti-APOA2 protein non-terminus antibody). For example, the amount of the APOA2-ATQ protein can be measured by sandwich ELISA using the anti-APOA2-ATQ terminus antibody as a labeled antibody and the anti-APOA2-ATQ non-terminus antibody as an immobilized antibody. Moreover, the amount of the APOA2-AT protein can be measured by sandwich ELISA using the anti-APOA2-AT terminus antibody as an immobilized antibody and the anti-APOA2-AT non-terminus antibody as a labeled antibody. Anti-APOA2 protein non-terminus antibodies are commercially available from Abcam PLC, Fitzgerald Industries International, and the like, and such commercially available products may be used.

2-2. Determining Process

The "determining process" is a process of determining (or evaluating) in vitro the pathology of biliary tract cancer based on the amounts of the proteins measured in the process of measuring the markers for the detection of biliary tract cancer described above. The measured markers for the detection of biliary tract cancer, that is, the amounts of the APOA2 protein variants (the amounts of the APOA2-ATQ protein and the APOA2-AT protein) in a body fluid sample from a test subject are determined, detection of biliary tract cancer is carried out, and then the presence of biliary tract cancer is determined, or the risk of biliary tract cancer is evaluated. This process comprises three steps of the first, second, and third steps. Each of the steps will be described in detail below.

(First Step)

In the first step, the amount of the APOA2-ATQ protein in a body fluid sample from a test subject is measured by using the anti-APOA2-ATQ terminus antibody which specifically binds to the C-terminal region of the APOA2-ATQ protein consisting of the amino acid sequence represented by SEQ ID NO: 1, and the anti-APOA2-ATQ non-terminus antibody which binds to the amino acid sequence excluding the C-terminal region.

(Second Step)

Next, in the second step, the amount of the APOA2-AT protein is measured by using the anti-APOA2-AT terminus antibody which specifically binds to the C-terminal region of the APOA2-AT protein consisting of the amino acid sequence represented by SEQ ID NO: 2, and the anti-APOA2-AT non-terminus antibody which binds to the amino acid sequence excluding the C-terminal region. The C-terminal regions of the APOA2-ATQ protein and the APOA2-AT protein, herein, desirably have sequences comprising 6 or more consecutive amino acids including each C-terminus. The amounts of the APOA2 protein variants can be measured by, for example but not limited to, ELISA. Furthermore, the anti-APOA2-ATQ non-terminus antibody, which is used in combination with the anti-APOA2-ATQ terminus antibody in the first step, and the anti-APOA2-AT non-terminus antibody, which is used in combination with anti-APOA2-AT terminus antibody in the second step, may be identical to the anti-APOA2 protein non-terminus antibody. For example, the anti-APOA2-AT non-terminus antibody may be used in the first step, or, alternatively, the anti-APOA2-ATQ non-terminus antibody may be used in the second step.

(Third Step)

In the third step, the measured amount of the APOA2-ATQ protein obtained in the first step and the measured amount of the APOA2-AT protein obtained in the second step are inputted into a prescribed discriminant function to obtain a discriminant value in the test subject and, if the discriminant value is statistically significantly different compared to the discriminant value in a normal subject, the test subject is affected with biliary tract cancer. The discriminant function used in this step can be established by the method described below.

Alternatively, a test subject may be conveniently determined to be affected with biliary tract cancer even if a discriminant value is not obtained but the amount of either the APOA2-ATQ protein or the APOA2-AT protein in a sample collected from the test subject is statistically significantly different, and specifically the measured amount is likewise significantly smaller, compared to the amount in a sample collected from a normal subject.

The method of detecting biliary tract cancer according to embodiments of the present invention may be combined to perform a discrimination task with a known biliary tract cancer marker(s) in a body fluid sample of the test subject and/or other discrimination methods. As the known biliary tract cancer marker, for example, the sialyl Lewis-A antigen "CA19-9" (Carbohydrate Antigen 19-9) and/or a mucin-like glycoprotein "DU-PAN-2" (Pancreatic cancer-associated antigen-2) can be used (Rinsho Kensa Data Book, 2013-2014, Humimaro Takaku, Editor-in-chief, Igaku-Shoin Ltd., p.636-638). In the identification of biliary tract cancer, the reference value is not more than 37 (U/mL) for CA19-9 and is not more than 150 (U/mL) for DU-PAN-2. The amounts of CA19-9 and DU-PAN-2 can be measured by, for example but not limited to, ELISA.

The method of detecting biliary tract cancer according to embodiments of the present invention may be used in combination with other APOA2 protein variants such as the APOA2-A protein, or the total amount of the APOA2 proteins. Such an aspect is also included in embodiments of the present invention.

The term "normal subject" refers to an individual who at least is not affected with biliary tract cancer, preferably a healthy individual. Furthermore, the normal subject should be the same organism species as the test subject. For example, when a test subject examined for the detection is a human (a subject), a normal subject should also be a human (hereinafter in this specification, referred to as "healthy subject"). Preferably, the physical conditions of the normal subject are identical or similar to those of the test subject. In the case of human, for example, physical conditions include race, gender, age, height, weight and the like.

The quantity of the markers for the detection of biliary tract cancer in body fluid of the normal subject is preferably measured by a method similar to the quantification method in the process of measuring markers for the detection of biliary tract cancer described above. The quantity of the markers for the detection of biliary tract cancer in body fluid of the normal subject may be measured every time the quantity of the markers for the detection of biliary tract cancer in body fluid of the test subject is measured, or the previously measured quantity of the markers for the detection of biliary tract cancer may be used. Particularly, it will be convenient to measure in advance the quantity of the markers for the detection of biliary tract cancer in the normal subjects under various physical conditions and to enter those values into a computer for database purpose, because the quantity of the markers for the detection of biliary tract cancer in a normal subject, who has optimal physical conditions for the comparison with a test sample, will be readily available once the physical conditions of the test subject are entered into the computer.

In this specification, the phrase "statistically significant" refers to, for example, the case where the error probability (significance level) for an obtained value is small and is specifically at the level of $p<0.05$, $p<0.01$, or $p<0.001$. The term "p" or "p-value" herein refers to the possibility in a statistical test where a hypothesis is true by chance in the context of the hypothesized distribution of statistics. Accordingly, a smaller "p" or "p-value" means that the hypothesis is more likely to be true. The phrase "statistically significantly different" represents here that there is a significant difference between both test and normal subjects when the test subject and the normal subject are compared for the quantity of the markers for the detection of biliary tract cancer obtained from each of them, or for the difference in the discriminant value obtained by inputting the values into the discriminant function. When the test subject is statistically significantly different compared to the normal subject, the test subject will be evaluated to be affected with biliary tract cancer. A test method for statistical processing is not particularly limited but a known method of test, with which a decision of significance or lack or significance can be made, may be appropriately employed. For example, a Student's t-test, a multiple-comparison test, or the like may be employed.

In this specification, the "discriminant function" is a formula established by multivariate analysis, which is characterized by a set of one or more values and finally calculates a discriminant value. The "multivariate analysis" is a mathematical procedure using, in this specification, measured values of the markers for the detection of biliary tract cancer to establish a discriminant function. Moreover, in the specification, the "set of values" refers to a combination or range of values representing the features of the markers for the detection of biliary tract cancer. The set of values and the properties of the values included therein are dependent on the types of the features present in the markers for the detection of biliary tract cancer and the multivariate analysis employed to establish a discriminant function that defines the set of values.

In this specification, the term "discriminant value" refers to a value calculated from a discriminant function, which can be used as an index for predicting whether a test subject is likely to be affected with biliary tract cancer. In one specific example, a test subject can be predicted to be affected with biliary tract cancer by a discriminant value. In another example, a test subject can be predicted not to be affected with biliary tract cancer by another discriminant value.

A discriminant function can be established by multivariate analysis using a data analysis algorithm. Examples of the data analysis algorithm that can be used for the establishment of the discriminant function include generalized linear model including logistic regression analysis, neural network, support vector machine (SVM), discriminant analysis, nonparametric approaches, PLS (Partial Least Squares), decision tree, principal component analysis, generalized additive model, fuzzy logic, SOM (Self-organizing maps), or genetic algorithm. Among them, logistic regression analysis, neural network, SVM, or discriminant analysis is preferable. However, the data analysis algorithm is not limited to these data analysis algorithms. The details of these statistical methods are found in the following references: Ruczinski, I. et al., 2003, Journal of Computational and Graphical Statistics, 12: 475-511; Friedman, J., Journal of the American Statistical Association, 1989, 84: 165-175; Hastie, T. et al., 2001, The Elements of Statistical Learning, Springer Series in Statistics; Breiman, L., 1984, Classification and regression trees, Chapman and Hall; Breiman, L., 2001, Machine Learning, 45: 5-32; Pepe, M., 2003, The Statistical Evaluation of Medical Tests for Classification and Prediction, Oxford Statistical Science Series; and Duda, R., 2000, Pattern Classification, 2nd ed., Wiley Interscience.

In embodiments of the present invention, the analysis using the discriminant function is carried out by the following steps. First, an event to be discriminated is regarded as a response variable. The "response variable" is an event to be discriminated according to a discriminant function. In embodiments of the present invention, it corresponds to the presence and absence of biliary tract cancer in a test subject. For example, in the case of logistic regression analysis, the response variable is coded as "1" for the case where the test subject is a biliary tract cancer patient and "0" for the case where the test subject is a healthy subject. Next, the explanatory variable to predict the response variable is established. The "explanatory variable" is a variable in a discriminant function used to predict the response variable. For example, in the case of logistic regression analysis, the measured values of the markers for the detection of biliary tract cancer, that is, of the APOA2-ATQ protein and the APOA2-AT protein can be established as explanatory variables. Next, a discriminant function including the explanatory variables in combination is developed by using any of the aforementioned data analysis algorithms to calculate a discriminant value. On the basis of the obtained discriminant value, prediction is performed on the event to be discriminated. For example, in the case of logistic regression analysis, the test subject may be predicted to be a biliary tract cancer patient (i.e., "1") or normal subject (i.e., "0") according to the discriminant value. Finally, the result of the prediction on the event and the value of the response variable are compared to evaluate the performance of the discriminant function in the discrimination. The "performance in discrimination" here refers to an index which reflects how accurately the event to be discriminated was successfully predicted. In the context of the performance in discrimination, results of discrimination (sensitivity, specificity) from case data or AUC values can be used. Preferably, the presence of biliary tract cancer is determined, or the risk of biliary tract cancer is evaluated, on the basis of a discriminant value derived from the discriminant function.

In this specification, the term "AUC (area under the curve) value" refers to the area under the curve of a receiver operating characteristic (ROC curve), which serves as an index to determine the precision of a method for prediction, discrimination, detection, or diagnosis to classify patients into positive and negative groups. In these curves, with regard to the results from a method to be evaluated, the true positive rate (sensitivity) at which a positive result occurs in positive patients and the value of one minus the probability (specificity) that a negative result occurs in negative patients (i.e., false positive rate) are plotted.

In this specification, the term "sensitivity" means the value of (number of true positive)/(number of true positive+ number of false negative). With a higher sensitivity, biliary tract cancer can be detected earlier, leading to the complete resection of a lesion or reduction in recurrence rate.

In this specification, the term "specificity" means the value of (number of true negative)/(number of true negative+number of false positive). With a higher specificity, the implementation of unnecessary additional tests, due to a false identification of a normal subject as a biliary tract cancer patient, will be prevented, leading to reduced burden on patients and decreased medical cost.

A method for analyzing a test subject for the presence of biliary tract cancer with a discriminant function will be specifically described below, which is based on logistic regression analysis and uses measured values of the APOA2 protein variants.

2-2-1. Discrimination Based on Logistic Regression Analysis

A method using logistic regression analysis to obtain a discriminant function can be employed as an analytical procedure to determine the presence of and evaluate the risk of biliary tract cancer.

First, all test subjects are divided to two groups according to the clinical information: biliary tract cancer patients and normal subjects. The response variable is coded as "1" for biliary tract cancer patient and "0" for normal subject. Next, a discriminant function is established from the measured values of two APOA2 protein variants obtained from the biological samples having the clinical information described above. The discriminant function may be preliminarily established as a logistic regression equation which includes the measured values of the APOA2-ATQ protein and the APOA2-AT protein as the explanatory variable, and/or the product of the measured value of the APOA2-AT protein and the measured value of the APOA2-ATQ protein as a variable. The validity of the logistic regression equation as a discriminant function can be evaluated by using an index such as the AIC (Akaike information criterion) value or the Schwarz's BIC value, both of which are included in the category of the maximum likelihood method.

Formulae including as explanatory variables the measured value of the APOA2-ATQ protein, the measured value of the APOA2-AT protein, and/or the product of the measured value of the APOA2-AT protein and the measured value of the APOA2-ATQ protein, as in the Formulae 1, 2 and 3, can be used as a logistic regression equation:

$$a \times (APOA2\text{-}ATQ) + b \times (APOA2\text{-}AT) + d, \quad \text{Formula 1:}$$

$$a \times (APOA2\text{-}ATQ) + b \times (APOA2\text{-}AT) + c \times (APOA2\text{-}ATQ) \times (APOA2\text{-}AT) + d, \quad \text{Formula 2:}$$

$$c \times (APOA2\text{-}ATQ) \times (APOA2\text{-}AT) + d, \quad \text{Formula 3:}$$

(in the Formulae 1 to 3, each of a, b, c and d is an optional real number except zero, (APOA2-ATQ) represents the measured value of the APOA2-ATQ protein, and (APOA2-AT) represents the measured value of the APOA2-AT protein).

In the cases where a discriminant function has been obtained as a logistic regression equation, the measured value of either the APOA2-ATQ protein or the APOA2-AT protein obtained from a test subject and a normal subject is inputted into the logistic regression equation to obtain a discriminant value and the obtained discriminant values may be compared and then the test subject may be affected with biliary tract cancer. For example, when the test subject is statistically significantly different from the normal subject as described above and the discriminant value of the test subject is equal to or less than two thirds of, more preferably a half of, further preferably one quarter of, the discriminant value of the normal subject, the test subject may be affected with biliary tract cancer.

3. Detection Kit for Biliary Tract Cancer

The third aspect of embodiments of the present invention is a detection kit for biliary tract cancer.

In this specification, the term "a detection kit for biliary tract cancer" refers to a kit used directly or indirectly to evaluate the presence or absence of biliary tract cancer, severity of biliary tract cancer, improvement of symptoms of biliary tract cancer, or its degree, or to screen candidate substances useful for the prevention, improvement of symptoms, or treatment of biliary tract cancer.

The kit according to this aspect encompasses, as its components, substances which can specifically recognize and bind to APOA2 protein variants, preferably the two APOA2 protein variants represented by SEQ ID NOs: 1 and 2, which show variable expression in relation of the pathology of biliary tract cancer in a body fluid sample, particularly in blood, serum, or plasma. Specifically, for example, anti-APOA2 protein terminus antibodies and the like, or fragments or chemically modified derivatives thereof are included. These antibodies may be bound to the solid carrier as described above and, in this case, preferably bound to the test strip as described above. In addition, for example, labeled secondary antibodies, and, furthermore, substrates required for the detection of the labels, a carrier, a washing buffer, a sample dilution solution, enzyme substrates, a reaction stopping solution, purified APOA2 proteins as the standard reference substances, an instruction manual and the like may be included.

EXAMPLES

Embodiments of the present invention will be described more specifically by the following Examples. However, it should be understood that the following Examples are for illustration purpose only and do not limit the scope of the present invention.

Comparative Example 1: Identification of Biliary Tract Cancer with the Amount of the APOA2-ATQ Protein in Blood Plasma samples collected from 44 biliary tract cancer patients and 109 healthy subjects with informed consent at National Cancer Center Hospital were assayed by ELISA to detect the APOA2-ATQ protein in blood.

The measurement of the amount of the APOA2-ATQ protein in blood was carried out by sandwich ELISA using a POD-labeled anti-APOA2-ATQ terminus monoclonal antibody 7F2 and an anti-APOA2 protein non-terminus polyclonal antibody, which recognizes the region of the APOA2 protein, excluding the C-terminal region (Fitzgerald Industries International). The labeling of the antibody 7F2 with POD was carried out using the Peroxidase Labeling Kit-SH (Dojindo Laboratories Inc.) and the details of the labeling followed the appended protocol of the kit. An anti-APOA2 protein non-terminus polyclonal antibody solution in PBS was prepared at a concentration of 2 µg/mL and, then, 100 µL of the solution was dispensed into each well of a Nunc Immunoplate MaxiSorp plate (manufactured by Thermo Fisher Scientific Inc.) for the overnight immobilization. Next day, the above solution was discarded, 400 μL of PBS-T (0.05% Tween-20 in PBS) was added to each well for washing, and 400 μL of a blocking buffer solution (1% BSA and 0.05% Tween-20 in PBS) was added to each well and incubated at room temperature for one hour. Subsequently, the above solution was discarded to obtain an antibody-immobilized plate. Next, 100 μL of a plasma sample diluted with a dilution solution was added to each well to allow reaction at room temperature for one hour. In this case, the dilution factor was 10,000. After the antigen solution in each well was discarded, the well was washed with PBS-T, 100 μL of the POD-labeled antibody 7F2 diluted with the dilution solution to a concentration of 0.2 μg/mL was added to each well to allow reaction at room temperature for one hour. After washing with PBS-T (manufactured by Pierce), 100 μL of TMB solution was added to each well for an enzyme reaction, 100 μL of 0.5 N sulfuric acid was added to stop the reaction, and then the absorbance was measured at 450 nm. The concentration of the protein in blood was calculated based on the comparison of the obtained measured value to that from a recombinant human APOA2-ATQ protein antigen solution as a reference standard. In FIG. 1, a plot of the concentration of the protein in blood of the healthy subjects and the biliary tract cancer patients is shown. The distribution in the healthy subjects was overlapped with that in the biliary tract cancer patients, indicating the difficulty in discrimination between them. Next, the discrimination of healthy subject and biliary tract cancer patient was performed using the measured value of the APOA2-ATQ protein according to the statistical processing below. Logistic regression analysis was performed defining the response variable as "1" for biliary tract cancer patient and "0" for healthy subject and using the measured value of the APOA2-ATQ protein as the explanatory variable to obtain a discriminant function and an AUC value. This procedure showed an AUC value of 0.782, indicating a relatively low performance in the identification of biliary tract cancer.

Figure 2:
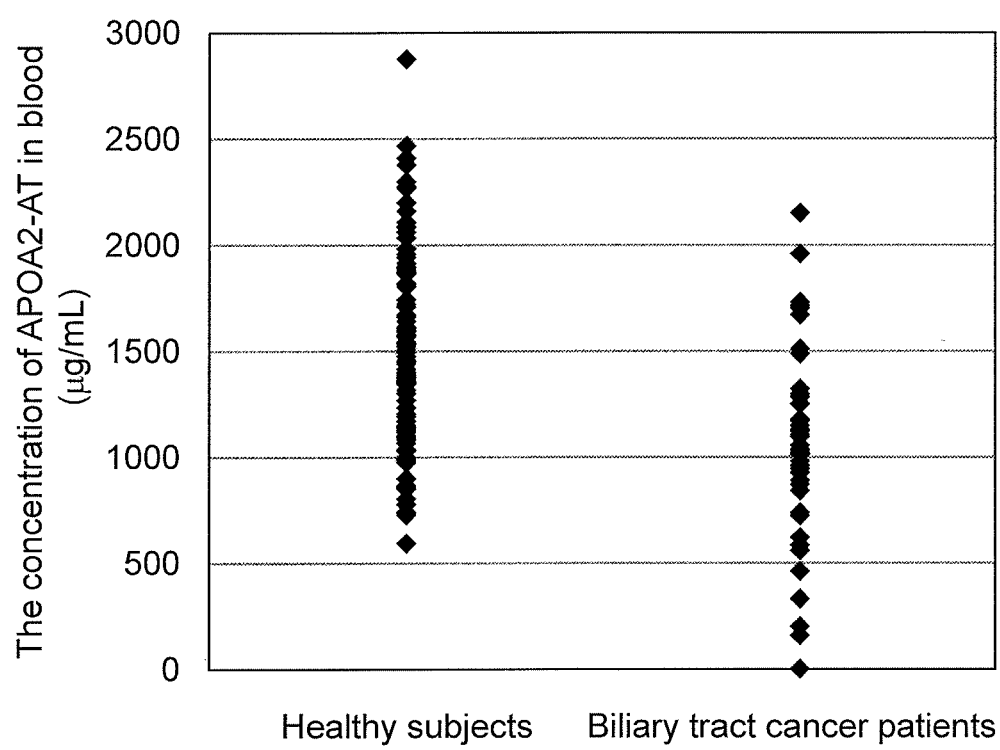
FIG. 2 shows a measurement of the concentration of the APOA2-AT protein contained in the plasma from 44 biliary tract cancer patients and 109 healthy subjects by sandwich ELISA using a polyclonal antibody specifically recognizing an amino acid sequence of the C-terminal region of the APOA2-AT protein (anti-APOA2-AT terminus polyclonal antibody) and an antibody specifically recognizing the amino acid sequence excluding the C-terminal region (anti-APOA2-AT non-terminus antibody).

Comparative Example 2: Identification of Biliary Tract Cancer with the Amount of the APOA2-AT Protein in Blood The measurement of the amount of the APOA2-AT protein in blood was carried out in the plasma samples similar to those in Comparative Example 1 by sandwich ELISA using an anti-APOA2-AT terminus polyclonal antibody and a POD-labeled anti-APOA2 protein non-terminus polyclonal antibody. The labeling of the anti-APOA2 protein non-terminus polyclonal antibody with POD and the sandwich ELISA were performed similarly to those in Comparative Example 1. The concentration of the protein in blood was calculated based on the comparison of the obtained measured value to that from a recombinant human APOA2-AT protein antigen solution as a reference standard. Moreover, the dilution factor for plasma was 6,000. In FIG. 2, a plot of the concentration of the protein in blood of the healthy subjects and the biliary tract cancer patients is shown. The distribution in the healthy subjects was overlapped with that in the biliary tract cancer patients, indicating the difficulty in discrimination between them. Next, the discrimination of healthy subject and biliary tract cancer patient was performed using the measured value of the APOA2-AT protein according to the statistical processing below. Logistic regression analysis was performed to obtain a discriminant function and an AUC value, in which the response variable was defined as "1" for biliary tract cancer patient and "0" for healthy subject and the measured value of the APOA2-AT protein was used as the explanatory variable. This procedure showed an AUC value of 0.770, indicating a relatively low performance in the identification of biliary tract cancer.

Figure 3:
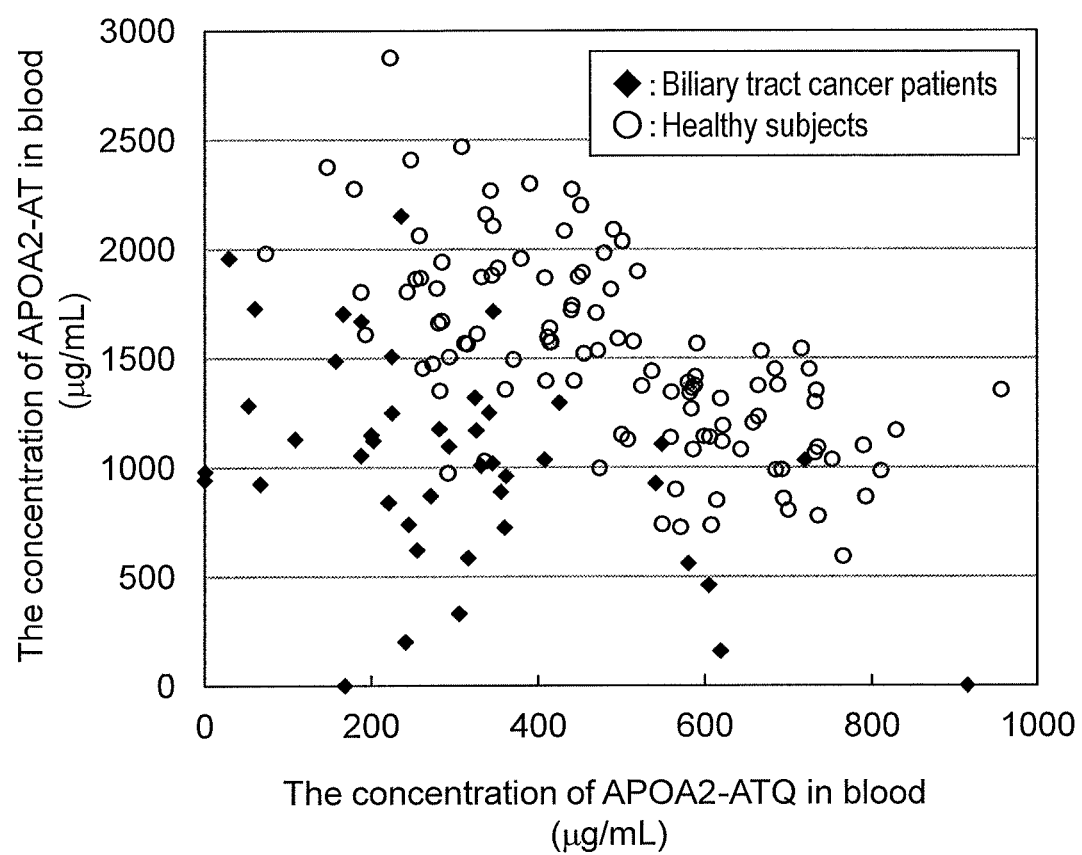
FIG. 3 shows the concentrations of two APOA2 protein variants (the APOA2-ATQ protein and the APOA2-AT protein) contained in the plasma from 44 biliary tract cancer patients and 109 healthy subjects in a scatter plot.
Figure 4:
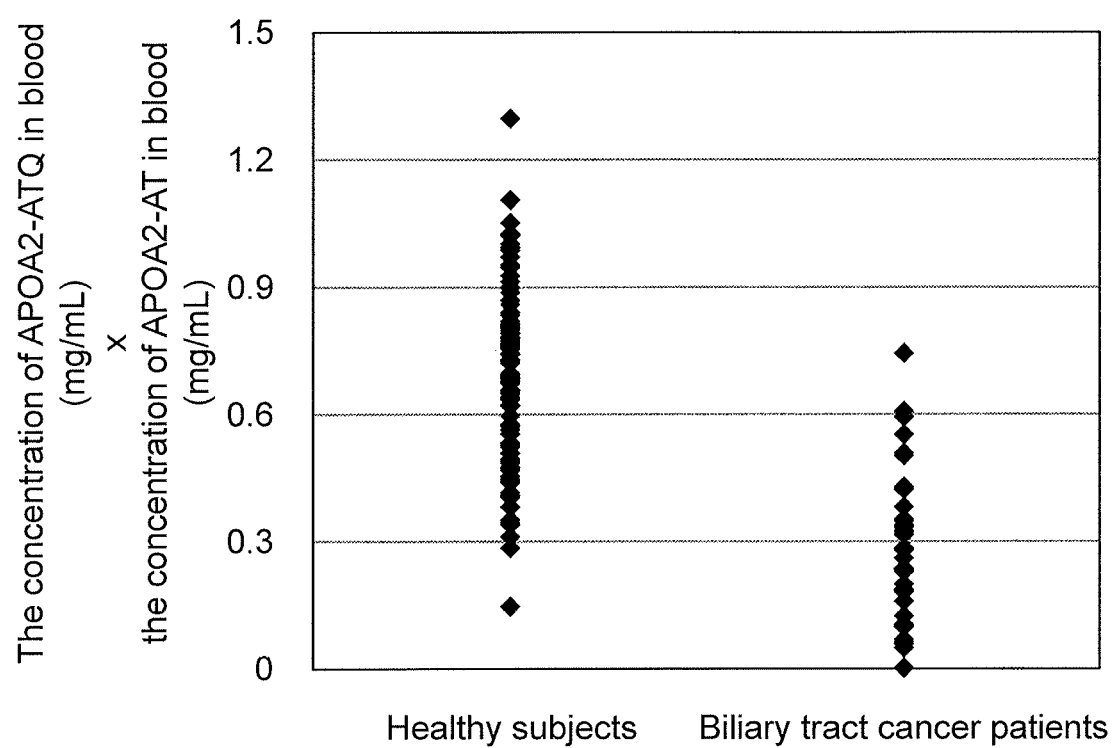
FIG. 4 shows the product of the concentrations of two APOA2 protein variants (the APOA2-ATQ protein and the APOA2-AT protein) contained in the plasma from 44 biliary tract cancer patients and 109 healthy subjects in a plot.

Example 1: Identification of Biliary Tract Cancer Based on the Product of the Amounts of the APOA2-ATQ Protein in Blood and the APOA2-AT Protein in Blood The results of Comparative Examples 1 and 2 indicated that the discrimination of biliary tract cancer patient and healthy subject using the measured amount of each of the APOA2 protein variants (APOA2-ATQ and APOA2-AT) had a low performance in the discrimination. Thus, the identification of biliary tract cancer was next attempted with a combination of the amounts of the above two APOA2 protein variants. In FIG. 3, a scatter plot of the concentrations of the APOA2-ATQ protein and the APOA2-AT protein in blood obtained in Comparative Examples 1 and 2, respectively, is shown. The result indicated that the difference in distribution between the healthy subjects and the biliary tract cancer patients was shown in the scatter plot. In FIG. 4, with regard to the healthy subjects and the biliary tract cancer patients, a plot of the product of the concentrations of the APOA2-ATQ protein and the APOA2-AT protein is shown. In the figure, the distributions corresponding to the healthy subjects and the biliary tract cancer patients are separated enough to be easily distinguished, as compared with those in FIGS. 1 and 2.

Next, the discrimination of healthy subject and biliary tract cancer patient was performed using the product of the measured amounts of the two APOA2 protein variants according to the statistical processing below. Logistic regression analysis was performed to obtain a discriminant function and an AUC value, in which the response variable was defined as "1" for biliary tract cancer patient and "0" for healthy subject and the product of the measured values of the two APOA2 protein variants obtained in Comparative Examples 1 and 2 was used as the explanatory variable. The yielded discriminant function was as shown below.

$$c \times [(APOA2\text{-}ATQ) \times (APOA2\text{-}AT)] + d, \quad \text{Formula 3:}$$

wherein each of c and d is an optional real number except zero, APOA2-ATQ represents the measured value of the APOA2-ATQ protein, and APOA2-AT represents the measured amount of the APOA2-AT protein.

This procedure showed an AUC value of 0.937 and was consequently confirmed to show a very high accuracy in identification of biliary tract cancer as compared with that in Comparative Examples 1 and 2.

Example 2: Identification of Biliary Tract Cancer with a Combination of the Amounts of the APOA2-ATQ Protein in Blood and the APOA2-AT Protein in Blood The discrimination of healthy subject and biliary tract cancer patient was performed using the measured amounts of APOA2 protein variants, namely the APOA2-ATQ protein and the APOA2-AT protein, according to the statistical processing below. Logistic regression analysis was performed to obtain a discriminant function and an AUC value, in which the response variable was defined as "1" for biliary tract cancer patient and "0" for healthy subject and the measured values of the two APOA2 protein variants (the APOA2-ATQ protein and the APOA2-AT protein) obtained in Comparative Examples 1 and 2 were used as the explanatory variable. The yielded discriminant function was as shown below.

a×(APOA2-ATQ)+b×(APOA2-AT)+d,   Formula 1:

wherein each of a, b and d is an optional real number except zero, APOA2-ATQ represents the measured value of the APOA2-ATQ protein, and APOA2-AT represents the measured amount of the APOA2-AT protein.

This procedure showed an AUC value of 0.943 and was consequently confirmed to show a very high accuracy in identification of biliary tract cancer as compared with that in Comparative Examples 1 and 2.

Example 3: Identification of Biliary Tract Cancer the Amount of APOA2-ATQ Protein in Blood, the Amount of APOA2-AT Protein in Blood and the Product of the Amount of the APOA2-AT Protein in Blood The discrimination of healthy subject and biliary tract cancer patient was performed using the measured amounts of APOA2 protein variants, namely the APOA2-ATQ protein and the APOA2-AT protein, and the product thereof according to the statistical processing below. Logistic regression analysis was performed to obtain a discriminant function and an AUC value, in which the response variable was defined as "1" for biliary tract cancer patient and "0" for healthy subject the measured values of the two APOA2 protein variants (the APOA2-ATQ protein and the APOA2-AT protein) obtained in Comparative Examples 1 and 2 and the product thereof were used as the explanatory variable. The yielded discriminant function was as shown below.

a×(APOA2-ATQ)+b×(APOA2-AT)+c×[(APOA2-ATQ)×(APOA2-AT)]+d,   Formula 2:

wherein each of a, b, c and d is an optional real number except zero, APOA2-ATQ represents the measured value of the APOA2-ATQ protein, and APOA2-AT represents the measured amount of the APOA2-AT protein.

Table 1 shows the AUC values and the calculated results of discrimination (sensitivity, specificity) from case data in the obtained discriminant function, and those results obtained in Comparative Examples 1 and 2 and Examples 1 and 2. In cases where the measured value of either APOA2-ATQ protein or the APOA2-AT protein was used as the explanatory variable, the sensitivity was 22% under the condition where the specificity was 97%. On the other hand, in cases where the product of the measured values of the APOA2-ATQ protein and the APOA2-AT protein was used as the explanatory variable, the sensitivity was 65%. In cases where the measured values of the APOA2-ATQ protein and the APOA2-AT protein were used as the explanatory variable, the sensitivity was 70%. Furthermore, when the measured values of the APOA2-ATQ protein and the APOA2-AT protein and the product thereof were used as the explanatory variable, the AUC value was increased to 0.946 and the sensitivity was also increased to 72% at the same time. These results confirmed that detection of biliary tract cancer with higher sensitivity as compared with that in Comparative Examples 1 and 2 was possible.

TABLE 1

| Explanatory variable | AUC | Sensitivity: % (number of subjects) | Specificity: % (number of subjects) |
|---|---|---|---|
| ATQ | 0.782 | 22 (10) | 97 (106) |
| AT | 0.770 | 22 (10) | 97 (106) |
| AT × ATQ | 0.937 | 65 (29) | 97 (106) |
| AT, ATQ | 0.943 | 70 (31) | 97 (106) |
| ATQ, AT, AT × ATQ | 0.946 | 72 (32) | 97 (106) |

The results of discrimination toward 44 biliary tract cancer patients and 109 healthy subjects are shown. ATQ and AT represent the amounts of the APOA2-ATQ protein and the APOA2-AT protein, respectively, identified in ELISA, and AT×ATQ represents the product thereof.

Comparative Example 3: Identification of Early Biliary Tract Cancer with CA19-9

Identification of early biliary tract cancer was performed with CA19-9. Twelve out of the biliary tract cancer patients used in Example 1 were chosen as early biliary tract cancer patients classified as 0, IA, IB, IIA and IIB according to the staging of UICC (Unio Internationalis Contra Cancrum) and the discrimination was performed on those 12 patients and the 109 healthy subjects. The discrimination using CA19-9 was performed as described below. The plasma collected from subjects was measured for the amount of CA19-9 by an immunological method. Typically, when the discrimination of healthy subject and biliary tract cancer patient is performed with CA19-9, an amount of not more than 37 (U/mL) is considered to be the reference value. In the discrimination, the amount of CA19-9 below the reference value corresponds to healthy subject, while the amount above the reference value corresponds to biliary tract cancer patient (Rinsho Kensa Data Book, 2013-2014, Humimaro Takaku, Editor-in-chief, Igaku-Shoin Ltd., p.636-637). In this Comparative Example, the discrimination of biliary tract cancer and healthy subjects was performed with CA19-9 on the basis of the above-described reference value. Consequently, in the context of the performance in identification of biliary tract cancer, the sensitivity was 41% (under a specificity of 95%), confirming a low performance in the identification of biliary tract cancer.

Example 4: Identification of Early Biliary Tract Cancer with APOA2

The identification of early biliary tract cancer was performed with the measured amounts of APOA2 protein variants, namely the APOA2-ATQ protein and the APOA2-AT protein. The same early biliary tract cancer patients as in Comparative Example 3 were used. In this procedure, the same discriminant function as used in Example 3 for the discrimination of healthy subject and biliary tract cancer patient (using a combination of the measured value of APOA2-ATQ protein, the measured value of APOA2-AT protein, and the product of the measured values of the APOA2-ATQ protein and the APOA2-AT protein) was used for the discrimination. Consequently, in the context of the performance in discrimination, the sensitivity was 58% (under a specificity of 97%), confirming that the detection of biliary tract cancer with higher accuracy as compared with the discrimination method using CA19-9 was possible.

Accordingly, the results of Examples 1 to 4 indicated that the present invention is useful in the detection of biliary tract cancer, including the detection of early biliary tract cancer (at the stages I and II) which has been considered difficult, with high sensitivity on the basis of the measured amounts of APOA2 protein variants analyzed by using a discriminant function.

According to embodiments of the present invention, high-throughput detection and early detection of biliary tract cancer with a simple and non-invasive method will be possible.

All publications, patents and patent applications cited in this specification shall be directly incorporated in this specification by reference.

The invention claimed is:

1. A method for detecting biliary tract cancer, the method comprising:
   determining an amount of an APOA2-ATQ protein and APOA2-AT protein present in a body fluid from a test subject and a normal subject by an immunological method using an anti-APOA2-ATQ terminus antibody which specifically binds to the C-terminal region of the APOA2-ATQ protein consisting of the amino acid sequence which is SEQ ID NO: 1, an anti-APOA2-AT terminus antibody which specifically binds to the C-terminal region of the APOA2- AT protein consisting of the amino acid sequence which is SEQ ID NO: 2, and an anti-APOA2 non-terminus antibody which binds to the amino acid sequence of the APOA2-ATQ protein or the APOA2-AT protein, excluding the its C-terminal region,
   wherein the determining process comprises the following steps (a) to (d):
   (a) contacting step of
   contacting the APOA2-ATQ protein present in body fluid of the test subject and the normal subject with the anti-APOA2-ATQ terminus antibody and the anti-APOA2 non-terminus antibody, and
   contacting the APOA2-AT protein present in body fluid of the test subject and the normal subject with the anti-APOA2-AT terminus antibody and the anti-APOA2 non-terminus antibody;
   (b) measuring step of measuring
   an amount of the APOA2-ATQ protein binding to both the anti-APOA2 non-terminus antibody and the anti-APOA2-ATQ terminus antibody and
   an amount of the APOA2-AT protein binding to both the anti-APOA2 non-terminus antibody and the anti-APOA2-AT terminus antibody;
   (c) inputting to a logistic regression equation for a discriminant value, the measurement of the amounts of the APOA2-ATQ protein and the amounts of the APOA2-AT protein obtained in the step (b) to obtain a discriminant value of the test subject; and
   (d) comparing the discriminant value of the test subject with that the normal subject to determine that the test subject is affected with biliary tract cancer when the discriminant value of the test subject is statistically significantly different with that of the normal subject,
   wherein the anti-APOA2-ATQ terminus antibody has
   the CDR1, CDR2 and CDR3 of the heavy chain consisting of the amino acid sequences which are SEQ ID NOs: 4, 5 and 6, respectively, and
   the CDR1, CDR2 and CDR3 of the light chain consisting of the amino acid sequences which are SEQ ID NOs: 7, 8 and 9, respectively; or
   the CDR1, CDR2and CDR3 of the heavy chain consisting of the amino acid sequences which are SEQ ID NOs: 10, 11 and 12, respectively, and
   the CDR1, CDR2 and CDR3 of the light chain consisting of the amino acid sequences which are SEQ ID NOs: 13, 14 and 15, respectively; and
   the anti-APOA2 non-terminus antibody has
   the CDR1, CDR2 and CDR3 of the heavy chain consisting of the amino acid sequences which are SEQ ID NOs: 16, 17 and 18 respectively, and
   the CDR1, CDR2 and CDR3 of the light chain consisting of the amino acid sequences which are SEQ ID NOs: 19, 20 and 21, respectively; or
   the CDR1, CDR2 and CDR3 of the heavy chain consisting of the amino acid sequences which are SEQ ID NOs: 22, 23 and 24, respectively, and
   the CDR1, CDR2 and CDR3 of the light chain consisting of the amino acid sequences which are SEQ ID NOs: 25, 26 and 27, respectively.

2. The detection method according to claim 1, wherein each of the C-terminal regions of the APOA2-ATQ protein and the APOA2-AT protein comprises a sequence consisting of 6 or more consecutive amino acids including the C-terminus of the corresponding protein.

3. The method according to claim 1, wherein the logistic regression equation is any one of:

a×(APOA2-ATQ)+b×(APOA2-AT)+d, Formula 1:

a×(APOA2-ATQ)+b×(APOA2-AT)+c×[(APOA2-ATQ)×(APOA2-AT)]+d, and Formula 2:

c×[(APOA2-ATQ)×(APOA2-AT)]+d, Formula 3:

wherein each of a, b, c and d is an optional real number except zero, APOA2-ATQ represents the measured value of the APOA2-ATQ protein, and APOA2-AT represents the measurement of the amount of the APOA2-AT protein.

4. The method according to claim 3, wherein the discriminant value of the test subject obtained by the logistic regression equation is two thirds or less of the discriminant value of the normal subject.

5. The method according claim 1, wherein the body fluid is blood.

6. The detection method according to claim 1, wherein the biliary tract cancer is early biliary tract cancer.

7. A kit for detection of biliary tract cancer, comprising one or more of a monoclonal antibody or a fragment thereof selected from the group consisting of an anti-APOA2-ATQ terminus monoclonal antibody or a fragment thereof and an anti-APOA2 protein non-terminus monoclonal antibody or a fragment thereof, wherein the anti-APOA2-ATQ terminus monoclonal antibody has the CDR1, CDR2 and CDR3 of the heavy chain consisting of the amino acid sequences represented by SEQ ID NOs: 4, 5 and 6, respectively, and the CDR1, CDR2 and CDR3 of the light chain consisting of the amino acid sequences represented by SEQ ID NOs: 7, 8 and 9, respectively; or the CDR1, CDR2 and CDR3 of the heavy chain consisting of the amino acid sequences which are SEQ ID NOs: 10, 11 and 12, respectively, and the CDR1, CDR2 and CDR3 of the light chain consisting of the amino acid sequences which are SEQ ID NOs: 13, 14 and 15, respectively; and the anti-APOA2 protein non-terminus monoclonal antibody has the CDR1, CDR2 and CDR3 of the heavy chain consisting of the amino acid sequences represented by SEQ ID NOs: 16, 17 and 18 respectively, and the CDR1, CDR2 and CDR3 of the light chain consisting of the amino acid sequences represented by SEQ ID NOs: 19, 20 and 21, respectively; or the CDR1, CDR2 and CDR3 of the heavy chain consisting of the amino acid sequences which are SEQ ID NOs: 22, 23 and 24, respectively, and the CDR1, CDR2 and CDR3 of the light chain consisting of the amino acid sequences which are SEQ ID NOs: 25, 26 and 27, respectively.

8. The detection method according to claim 2, wherein the body fluid is blood.

9. The detection method according to claim 3, wherein the body fluid is blood.

10. The detection method according to claim 4, wherein the body fluid is blood.

11. The method according to claim 2, wherein the biliary tract cancer is early biliary tract cancer.

12. The method according to claim 3, wherein the biliary tract cancer is early biliary tract cancer.

13. The method according to claim 4, wherein the biliary tract cancer is early biliary tract cancer.

14. The method according to claim 5, wherein the biliary tract cancer is early biliary tract cancer.

\* \* \* \* \*

SEQUENCE LISTING

```
<160> NUMBER OF SEQ ID NOS: 29

<210> SEQ ID NO 1
<211> LENGTH: 77
<212> TYPE: PRT
<213> ORGANISM: Homo sapiens

<400> SEQUENCE: 1

Gln Ala Lys Glu Pro Cys Val Glu Ser Leu Val Ser Gln Tyr Phe Gln
1               5                   10                  15

Thr Val Thr Asp Tyr Gly Lys Asp Leu Met Glu Lys Val Lys Ser Pro
            20                  25                  30

Glu Leu Gln Ala Glu Ala Lys Ser Tyr Phe Glu Lys Ser Lys Glu Gln
        35                  40                  45

Leu Thr Pro Leu Ile Lys Lys Ala Gly Thr Glu Leu Val Asn Phe Leu
    50                  55                  60

Ser Tyr Phe Val Glu Leu Gly Thr Gln Pro Ala Thr Gln
65                  70                  75

<210> SEQ ID NO 2
<211> LENGTH: 76
<212> TYPE: PRT
<213> ORGANISM: Homo sapiens

<400> SEQUENCE: 2

Gln Ala Lys Glu Pro Cys Val Glu Ser Leu Val Ser Gln Tyr Phe Gln
1               5                   10                  15

Thr Val Thr Asp Tyr Gly Lys Asp Leu Met Glu Lys Val Lys Ser Pro
            20                  25                  30

Glu Leu Gln Ala Glu Ala Lys Ser Tyr Phe Glu Lys Ser Lys Glu Gln
        35                  40                  45

Leu Thr Pro Leu Ile Lys Lys Ala Gly Thr Glu Leu Val Asn Phe Leu
    50                  55                  60

Ser Tyr Phe Val Glu Leu Gly Thr Gln Pro Ala Thr
65                  70                  75

<210> SEQ ID NO 3
<211> LENGTH: 75
<212> TYPE: PRT
<213> ORGANISM: Homo sapiens

<400> SEQUENCE: 3

Gln Ala Lys Glu Pro Cys Val Glu Ser Leu Val Ser Gln Tyr Phe Gln
1               5                   10                  15

Thr Val Thr Asp Tyr Gly Lys Asp Leu Met Glu Lys Val Lys Ser Pro
            20                  25                  30

Glu Leu Gln Ala Glu Ala Lys Ser Tyr Phe Glu Lys Ser Lys Glu Gln
        35                  40                  45

Leu Thr Pro Leu Ile Lys Lys Ala Gly Thr Glu Leu Val Asn Phe Leu
    50                  55                  60
```

Ser Tyr Phe Val Glu Leu Gly Thr Gln Pro Ala
65                  70                  75

<210> SEQ ID NO 4
<211> LENGTH: 10
<212> TYPE: PRT
<213> ORGANISM: Artificial Sequence
<220> FEATURE:
<223> OTHER INFORMATION: antibody

<400> SEQUENCE: 4

Gly Tyr Thr Phe Thr Asn Tyr Trp Met His
1               5                   10

<210> SEQ ID NO 5
<211> LENGTH: 17
<212> TYPE: PRT
<213> ORGANISM: Artificial Sequence
<220> FEATURE:
<223> OTHER INFORMATION: antibody

<400> SEQUENCE: 5

Asn Ile Tyr Pro Gly Ser Gly Asn Thr Asn Tyr Asn Glu Lys Phe Lys
1               5                   10                  15

Ser

<210> SEQ ID NO 6
<211> LENGTH: 10
<212> TYPE: PRT
<213> ORGANISM: Artificial Sequence
<220> FEATURE:
<223> OTHER INFORMATION: antibody

<400> SEQUENCE: 6

Arg Tyr Gly Tyr Val Asp Trp Phe Ala Tyr
1               5                   10

<210> SEQ ID NO 7
<211> LENGTH: 16
<212> TYPE: PRT
<213> ORGANISM: Artificial Sequence
<220> FEATURE:
<223> OTHER INFORMATION: antibody

<400> SEQUENCE: 7

Arg Ser Ser Lys Ser Leu Leu Tyr Lys Asp Gly Lys Thr Tyr Leu Asn
1               5                   10                  15

<210> SEQ ID NO 8
<211> LENGTH: 7
<212> TYPE: PRT
<213> ORGANISM: Artificial Sequence
<220> FEATURE:
<223> OTHER INFORMATION: antibody

<400> SEQUENCE: 8

Leu Met Ser Thr Arg Ala Ser
1               5

<210> SEQ ID NO 9
<211> LENGTH: 9
<212> TYPE: PRT
<213> ORGANISM: Artificial Sequence
<220> FEATURE:
<223> OTHER INFORMATION: antibody

<400> SEQUENCE: 9

```
Gln Gln Leu Val Glu Tyr Pro Leu Thr
1               5

<210> SEQ ID NO 10
<211> LENGTH: 5
<212> TYPE: PRT
<213> ORGANISM: Artificial Sequence
<220> FEATURE:
<223> OTHER INFORMATION: antibody

<400> SEQUENCE: 10

Asn Tyr Gly Met Asn
1               5

<210> SEQ ID NO 11
<211> LENGTH: 17
<212> TYPE: PRT
<213> ORGANISM: Artificial Sequence
<220> FEATURE:
<223> OTHER INFORMATION: antibody

<400> SEQUENCE: 11

Trp Lys Asn Thr Tyr Thr Gly Glu Ser Thr Tyr Ala Asp Asp Phe Lys
1               5                   10                  15

Gly

<210> SEQ ID NO 12
<211> LENGTH: 11
<212> TYPE: PRT
<213> ORGANISM: Artificial Sequence
<220> FEATURE:
<223> OTHER INFORMATION: antibody

<400> SEQUENCE: 12

Arg Asp Gly Ser Lys Tyr Lys Ile Phe Asp Tyr
1               5                   10

<210> SEQ ID NO 13
<211> LENGTH: 12
<212> TYPE: PRT
<213> ORGANISM: Artificial Sequence
<220> FEATURE:
<223> OTHER INFORMATION: antibody

<400> SEQUENCE: 13

Arg Ala Ser Ser Ser Leu Ser Ser Ser Tyr Leu His
1               5                   10

<210> SEQ ID NO 14
<211> LENGTH: 7
<212> TYPE: PRT
<213> ORGANISM: Artificial Sequence
<220> FEATURE:
<223> OTHER INFORMATION: antibody

<400> SEQUENCE: 14

Ser Thr Ser Asn Leu Ala Ser
1               5

<210> SEQ ID NO 15
<211> LENGTH: 9
<212> TYPE: PRT
<213> ORGANISM: Artificial Sequence
<220> FEATURE:
<223> OTHER INFORMATION: antibody
```

```
<400> SEQUENCE: 15

Gln Gln Phe Ser Val Phe Pro Leu Thr
1               5

<210> SEQ ID NO 16
<211> LENGTH: 10
<212> TYPE: PRT
<213> ORGANISM: Artificial Sequence
<220> FEATURE:
<223> OTHER INFORMATION: antibody

<400> SEQUENCE: 16

Gly Tyr Thr Phe Thr Ser Tyr Trp Met His
1               5                   10

<210> SEQ ID NO 17
<211> LENGTH: 17
<212> TYPE: PRT
<213> ORGANISM: Artificial Sequence
<220> FEATURE:
<223> OTHER INFORMATION: antibody

<400> SEQUENCE: 17

Phe Ile Asn Pro Ser Thr Gly Tyr Thr Glu Asn Asn Gln Arg Phe Asn
1               5                   10                  15

Asp

<210> SEQ ID NO 18
<211> LENGTH: 10
<212> TYPE: PRT
<213> ORGANISM: Artificial Sequence
<220> FEATURE:
<223> OTHER INFORMATION: antibody

<400> SEQUENCE: 18

Arg Pro Tyr Asn Pro Tyr Ala Met Asp Tyr
1               5                   10

<210> SEQ ID NO 19
<211> LENGTH: 11
<212> TYPE: PRT
<213> ORGANISM: Artificial Sequence
<220> FEATURE:
<223> OTHER INFORMATION: antibody

<400> SEQUENCE: 19

Arg Ala Ser Gln Asp Thr Ser Asn Tyr Leu Asn
1               5                   10

<210> SEQ ID NO 20
<211> LENGTH: 7
<212> TYPE: PRT
<213> ORGANISM: Artificial Sequence
<220> FEATURE:
<223> OTHER INFORMATION: antibody

<400> SEQUENCE: 20

Tyr Thr Ser Arg Leu His Ser
1               5

<210> SEQ ID NO 21
<211> LENGTH: 9
<212> TYPE: PRT
<213> ORGANISM: Artificial Sequence
<220> FEATURE:
<223> OTHER INFORMATION: antibody
```

<400> SEQUENCE: 21

Gln Gln Gly Asn Thr Leu Pro Tyr Thr
1               5

<210> SEQ ID NO 22
<211> LENGTH: 10
<212> TYPE: PRT
<213> ORGANISM: Artificial Sequence
<220> FEATURE:
<223> OTHER INFORMATION: antibody

<400> SEQUENCE: 22

Gly Tyr Thr Phe Thr Ser Tyr Trp Met His
1               5                   10

<210> SEQ ID NO 23
<211> LENGTH: 17
<212> TYPE: PRT
<213> ORGANISM: Artificial Sequence
<220> FEATURE:
<223> OTHER INFORMATION: antibody

<400> SEQUENCE: 23

Phe Ile Asn Pro Ser Thr Gly Tyr Thr Glu Asn Asn Gln Asn Phe Lys
1               5                   10                  15

Glu

<210> SEQ ID NO 24
<211> LENGTH: 10
<212> TYPE: PRT
<213> ORGANISM: Artificial Sequence
<220> FEATURE:
<223> OTHER INFORMATION: antibody

<400> SEQUENCE: 24

Arg Thr Tyr Asn Pro Tyr Gly Met Asp Tyr
1               5                   10

<210> SEQ ID NO 25
<211> LENGTH: 11
<212> TYPE: PRT
<213> ORGANISM: Artificial Sequence
<220> FEATURE:
<223> OTHER INFORMATION: antibody

<400> SEQUENCE: 25

Arg Ala Ser Gln Asp Ile Ser Asn Tyr Leu Asn
1               5                   10

<210> SEQ ID NO 26
<211> LENGTH: 7
<212> TYPE: PRT
<213> ORGANISM: Artificial Sequence
<220> FEATURE:
<223> OTHER INFORMATION: antibody

<400> SEQUENCE: 26

Tyr Thr Ser Arg Leu Gln Ser
1               5

<210> SEQ ID NO 27
<211> LENGTH: 9
<212> TYPE: PRT
<213> ORGANISM: Artificial Sequence
<220> FEATURE:

```
<223> OTHER INFORMATION: antibody

<400> SEQUENCE: 27

Gln Gln Gly Asn Thr Leu Pro Tyr Thr
1               5

<210> SEQ ID NO 28
<211> LENGTH: 16
<212> TYPE: PRT
<213> ORGANISM: Homo sapiens

<400> SEQUENCE: 28

Val Asn Phe Leu Ser Tyr Phe Val Glu Leu Gly Thr Gln Pro Ala Thr
1               5                   10                  15

<210> SEQ ID NO 29
<211> LENGTH: 17
<212> TYPE: PRT
<213> ORGANISM: Homo sapiens

<400> SEQUENCE: 29

Val Asn Phe Leu Ser Tyr Phe Val Glu Leu Gly Thr Gln Pro Ala Thr
1               5                   10                  15

Gln
```